(12) United States Patent
Seo et al.

(10) Patent No.: US 10,815,275 B2
(45) Date of Patent: Oct. 27, 2020

(54) ANTIMICROBIAL PEPTOIDS WITH IMPROVED SELECTIVITY AND USE THEREOF

(71) Applicant: GWANGJU INSTITUTE OF SCIENCE AND TECHNOLOGY, Gwangju (KR)

(72) Inventors: Jiwon Seo, Gwangju (KR); Ho Yeon Nam, Gwangju (KR); Ji Eun Choi, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 0 days.

(21) Appl. No.: 16/357,634

(22) Filed: Mar. 19, 2019

(65) Prior Publication Data
US 2019/0284238 A1 Sep. 19, 2019

(30) Foreign Application Priority Data
Mar. 19, 2018 (KR) .................. 10-2018-0031584

(51) Int. Cl.
| | |
|---|---|
| *A61K 38/00* | (2006.01) |
| *C07K 7/06* | (2006.01) |
| *C07K 7/08* | (2006.01) |
| *A61P 31/04* | (2006.01) |

(52) U.S. Cl.
CPC ............. *C07K 7/08* (2013.01); *A61P 31/04* (2018.01); *C07K 7/06* (2013.01); *A61K 38/00* (2013.01)

(58) Field of Classification Search
CPC ........... A61K 38/00; A61P 31/04; C07K 7/06; C07K 7/08
USPC .......................................... 530/300; 514/1.1
See application file for complete search history.

(56) References Cited

U.S. PATENT DOCUMENTS

| | | | |
|---|---|---|---|
| 8,445,632 B2 * | 5/2013 | Barron ................ | C07K 5/0815 530/300 |
| 2012/0295838 A1 * | 11/2012 | Barron ................ | C07K 5/0815 514/2.4 |

FOREIGN PATENT DOCUMENTS

| | | |
|---|---|---|
| JP | 2011-511077 A | 4/2011 |
| WO | 2009/105167 A2 | 8/2009 |

OTHER PUBLICATIONS

Lee et al., "Effect of side chain hydrophobicity and cationic charge on antimicrobial activity and cytotoxicity of helical peptoids," Bioorganic & Medicinal Chemistry Letters, 28: 170-173. Available online Nov. 23, 2017. (Year: 2017).*
Food poisoning from Merck Manual, p. 1. Accessed Mar. 17, 2020. (Year: 2020).*
Cholera from Merck Manual, pp. 1-4. Accessed Mar. 17, 2020. (Year: 2020).*
Shigellosis, Bacillary Dysentery, from Merck Manual, pp. 1-4. Accessed Mar. 17, 2020. (Year: 2020).*
Pertussis from Merck Manual, pp. 1-6. Accessed Mar. 17, 2020. (Year: 2020).*
Tuberculosis from Merck Manual, pp. 1-18. Accessed Mar. 17, 2020. (Year: 2020).*
Typhoid Fever from Merck Manual, pp. 1-5. Accessed Mar. 17, 2020. (Year: 2020).*
Jiwon Seo et al., In Vivo Biodistribution and Small Animal PET of 64Cu-Labeled Antimicrobial Peptoids, Bioconjugate Chemistry, Apr. 9, 2012, pp. 1069-1079, Korea.
Korean Office Action for corresponding Korean application No. 10-2019-0031160 dated Jun. 5, 2020.

* cited by examiner

*Primary Examiner* — Julie Ha
(74) *Attorney, Agent, or Firm* — Hauptman Ham, LLP

(57) ABSTRACT

Antimicrobial peptoids with improved selectivity to bacteria and a use thereof are described. Specifically, the antimicrobial peptoids have high antimicrobial activity and greatly decreased toxicity to animal cells. The antimicrobial peptoids show excellent antimicrobial activity against bacteria and exhibit low cytotoxicity to animal cells due to altered degree of folding in helical structure or altered charge characteristics. Therefore, the antimicrobial peptoids have improved selectivity to bacteria, and thus can be usefully used as antimicrobial compositions.

11 Claims, 12 Drawing Sheets

ANTIMICROBIAL PEPTOIDS WITH IMPROVED SELECTIVITY AND USE THEREOF

CROSS-REFERENCE TO RELATED APPLICATIONS

This application claims the priority of Korean Patent Application No. 10-2018-0031584 filed on Mar. 19, 2018 in the Korean Intellectual Property Office, the disclosure of which is hereby incorporated by reference in its entirety.

BACKGROUND OF THE INVENTION

1. Field of the Invention

The present invention relates to antimicrobial peptoids with improved selectivity to bacteria and a use thereof. Specifically, the present invention relates to antimicrobial peptoids having increased antimicrobial activity and decreased toxicity to animal cells.

2. Description of the Related Art

Alexander Fleming (who was awarded the 1945 Nobel Prize in Physiology or Medicine) discovered penicillin in a blue mold in 1928, and penicillin has been used as a miracle antibiotic since 1942. Since then, human mortality caused by bacterial infection has declined sharply. Subsequently, various classes of antibiotics such as sulfonamide, tetracycline, quinolone, aminoglycoside, vancomycin, rifamycin, daptomycin, and carbapenem have been developed to treat various bacterial infections. However, due to abuse or misuse of antibiotics in hospitals and livestock farms, multidrug-resistant bacteria (MDR) have now become a factor that threatens human health all over the world. In particular, Gram-negative bacteria of *Acinetobacter* sp., *Pseudomonas* sp., and *Enterobacteriaceae* which are resistant to various antibiotics such as polymyxin and carbapenem have been reported. In the 2016 US Centers for Disease Control and Prevention (CDC) report, deaths of infected patients, due to emergence of pan-resistant bacteria which cannot be treated with any existing antibiotics, were reported. Emergence of such multidrug-resistant bacteria and rapid decrease in the number of newly developed antibiotics necessitate development of antibiotics having antimicrobial mechanisms differentiated from existing drugs.

Researches on new antibiotics have been carried out in order to kill multidrug-resistant bacteria. Researches and developments on natural antibiotics such as magainin-2, melittin, cathelicidin, and defensin which are naturally occurring have been conducted. These antimicrobial peptides showed excellent antimicrobial activity against multidrug-resistant bacteria in vitro. However, such peptides are formed by peptide bonds between natural amino acids, and thus are rapidly degraded by enzymes in vivo; and increased dose thereof leads to a toxicity problem. Thus, there have been difficulties in applying such peptides for clinical practice.

In recent years, researches on antimicrobial peptoids are underway, in which the antimicrobial peptoids have increased resistance against proteolysis by modification of peptide backbones of natural antibiotics which are naturally occurring. Antimicrobial peptoids, which mimic cationic and amphipathic structural features of natural antibiotics by alteration of side chain derivatives of peptides, have better pharmacokinetic properties and exhibit a more stable antimicrobial activity than natural antimicrobial peptides, due to remarkably delayed enzymatic hydrolysis in vivo (Seo et al. *Bioconjugate Chem.*, 1069 to 1079, 2012). However, existing antimicrobial peptoids exhibited cytotoxicity against mammalian cells such as NIH 3T3 mouse fibroblasts. Therefore, there is a need for researches on antimicrobial peptoids that have decreased toxicity against animal cells and increased selectivity.

SUMMARY OF THE INVENTION

Accordingly, the present inventors have conducted researches to develop antimicrobial peptoids having increased selectivity to bacteria. As a result, the present inventors have identified that peptoids, which have altered degree of folding in helical structure or have altered charge characteristics, show antimicrobial activity against bacteria and exhibit low cytotoxicity, and thus have completed the present invention.

In order to achieve the above object, the present invention provides a peptoid having any one formula selected from Formulae 1 to 5.

In addition, the present invention provides an antimicrobial composition, comprising the peptoid as an active ingredient.

Furthermore, the present invention provides an antimicrobial quasi-drug composition, comprising the peptoid as an active ingredient.

In addition, the present invention provides a pharmaceutical composition for preventing or treating a bacterial infection, comprising the peptoid as an active ingredient.

Due to altered degree of folding in helical structure or altered charge characteristics, the antimicrobial peptoids of the present invention show excellent antimicrobial activity against bacteria and exhibit low cytotoxicity to animal cells. Therefore, the antimicrobial peptoids of the present invention have improved selectivity to bacteria, and thus can be usefully used as antimicrobial compositions.

DESCRIPTION OF THE PREFERRED EMBODIMENTS

Figure 1A:
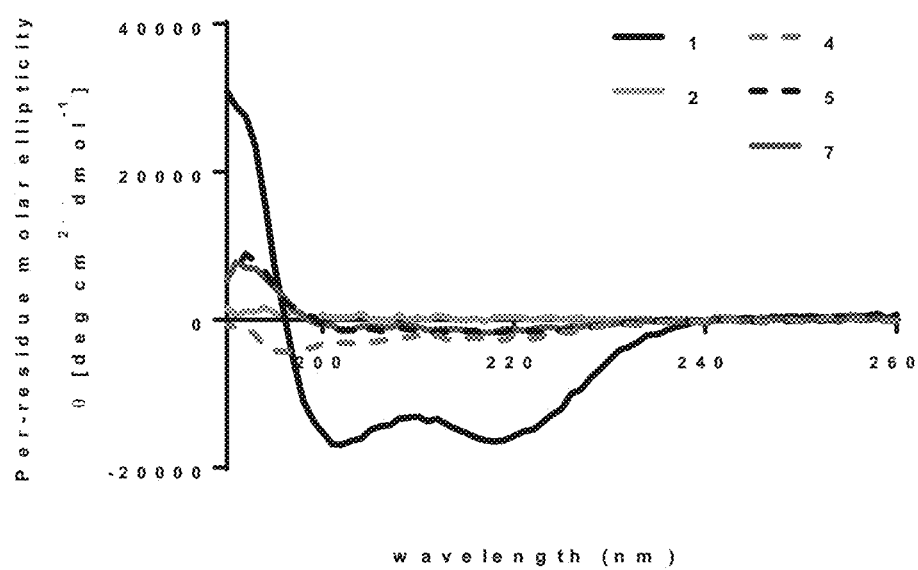
FIG. 1A is a diagram obtained by analyzing a degree of folding in helical structure of a single-Nspe peptoid in acetonitrile (solvent) using a circular dichroism spectropolarimeter.

Hereinafter, the present invention will be described in detail.

The present invention provides a peptoid having any one formula selected from the following Formulae 1 to 5:

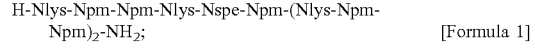
H-Nlys-Npm-Npm-Nlys-Nspe-Npm-(Nlys-Npm-Npm)$_2$-NH$_2$; [Formula 1]

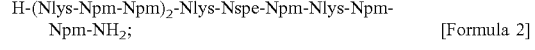
H-(Nlys-Npm-Npm)$_2$-Nlys-Nspe-Npm-Nlys-Npm-Npm-NH$_2$; [Formula 2]

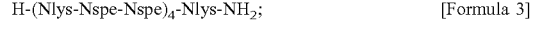
H-(Nlys-Nspe-Nspe)$_4$-Nlys-NH$_2$; [Formula 3]

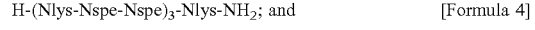
H-(Nlys-Nspe-Nspe)$_3$-Nlys-NH$_2$; and [Formula 4]

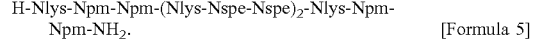
H-Nlys-Npm-Npm-(Nlys-Nspe-Nspe)$_2$-Nlys-Npm-Npm-NH$_2$. [Formula 5]

As used herein, the term "peptoid" refers to a peptide mimetic having an oligomeric form of N-alkylated glycine. Peptoids have a form which lacks a chiral center and amide hydrogen because a substituent (R) is attached to amine Unlike peptides, these peptoids are unnatural and are not easily degraded by proteolytic enzymes, so that the peptoids are highly stable in vivo. Thus, peptoids can overcome disadvantages of peptides that are readily degraded in vivo.

In addition, peptoids can be easily synthesized using solid-phase synthesis like peptides. It is possible to simply introduce a peptoid residue through a two-step reaction of bromoacetylation reaction and amine displacement reaction using, as a starting material, polymer beads having an amine group. A peptoid oligomer can be efficiently synthesized by repeating such a procedure.

The peptoids of the present invention were constructed by mimicking Pexiganan which is a synthetic antimicrobial peptide. The Pexiganan is an antimicrobial peptide consisting of 22 amino acids and is similar to magainins which are natural antimicrobial peptides isolated from the skin of an African clawed frog (Xenopus laevis). The peptoids of the present invention are shown in Table 1 below.

TABLE 1
| Classification [Formula] | Structural formula |
| --- | --- |
| [Formula 1] | 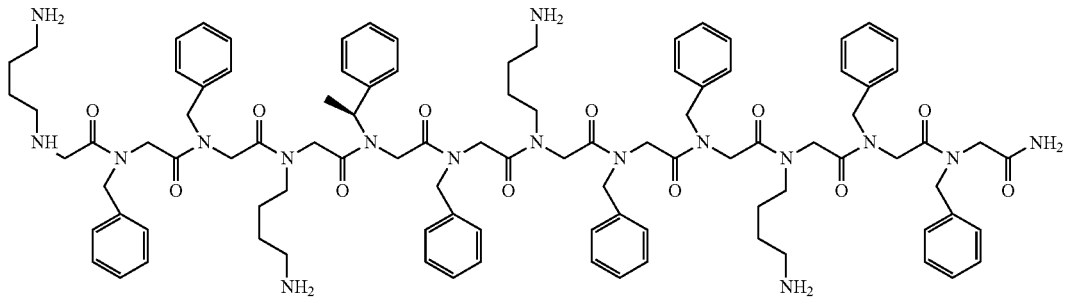 [SMILES: C[C@@H](c1ccccc1)N(CC(=O)N(CC(=O)N(CCCCN)CC(=O)N(CC(=O)N(CC(=O)N(CCCCN)CC(=O)N(CC(=O)N(CC(N)=O)Cc1ccccc1)Cc1ccccc1)Cc1ccccc1)Cc1ccccc1)Cc1ccccc1)C(=O)CN(CCCCN)C(=O)CN(Cc1ccccc1)C(=O)CN(Cc1ccccc1)C(=O)CNCCCCN] |
| [Formula 2] | 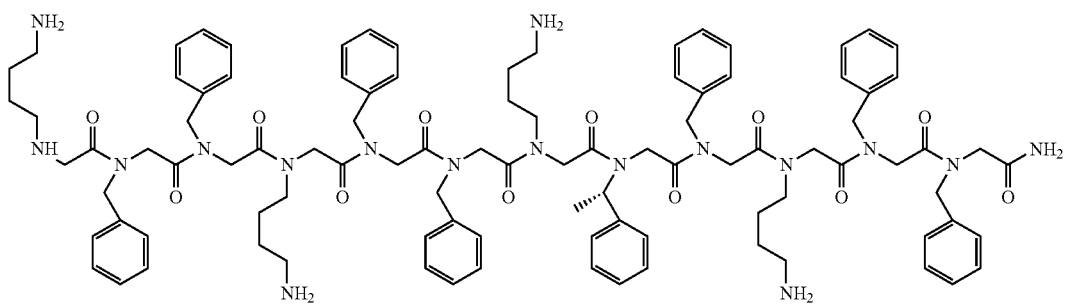 |
| [Formula 3] | 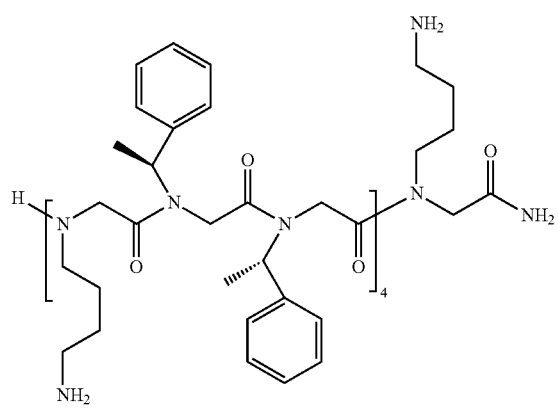 |
| [Formula 4] | 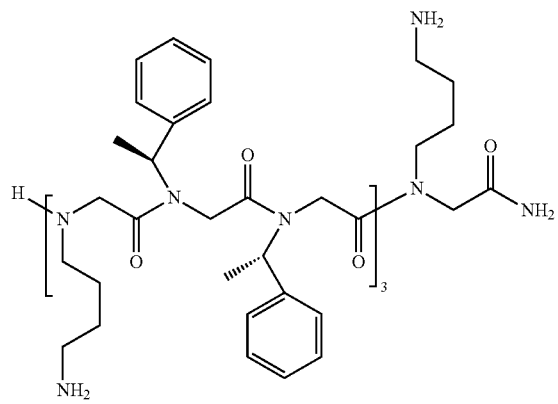 |

TABLE 1-continued

| Classification [Formula] | Structural formula |
|---|---|
| [Formula 5] | 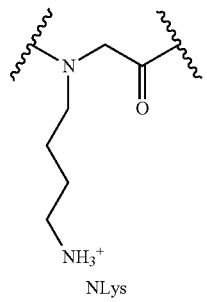 |

As used herein, the term "Nlys" means N-(4-aminobutyl)glycine. The Nlys has a structure represented by the following Formula 6.

[Formula 6]

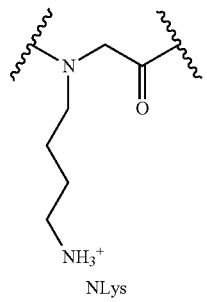

NLys

As used herein, the term "Npm" means N-(phenylmethyl)glycine. The Npm has a structure represented by the following Formula 7.

[Formula 7]

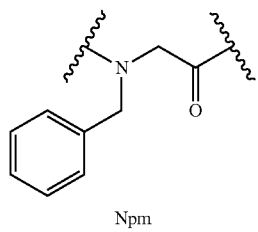

Npm

As used herein, the term "Nspe" means N-(S)-(1-phenylethyl)glycine. The Nspe has a structure represented by the following Formula 8.

[Formula 8]

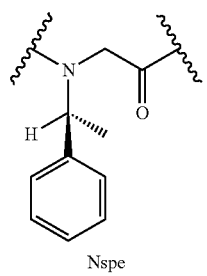

Nspe

The peptoids of the present invention have altered degree of folding in helical structure or altered charge characteristics in order to solve a cytotoxicity problem of existing antimicrobial peptoids. Specifically, in order to identify changes in activity of peptoids depending on alteration of degree of folding in helical structure, Peptoid NOS. 3 to 17 were synthesized which have altered degree of folding in helical structure (FIGS. 5 to 19). Among the Peptoid NOS. 3 to 17, Peptoid NOS. 5, 7, and 16 which have excellent antimicrobial activity and have decreased cytotoxicity were selected (Tables 5 to 8). In addition, in order to identify changes in activity of peptoids depending on alteration of charge characteristics, Peptoid NOS. 18 to 23 were synthesized which have altered charge characteristics (FIGS. 21 to 26). Among the Peptoid NOS. 18 to 23, Peptoid NOS. 22 and 23 which have excellent antimicrobial activity and have decreased cytotoxicity were selected (Tables 12 to 15).

Therefore, the peptoids of the present invention have excellent antimicrobial activity and have decreased cytotoxicity, and thus can be usefully used as antimicrobial compositions.

The present invention provides an antimicrobial composition, comprising the peptoid of the present invention as an active ingredient. The peptoid may exhibit antimicrobial activity against Gram-positive bacteria or Gram-negative bacteria.

As used herein, the term "antimicrobial" means an ability to resist bacteria and means any mechanism which is performed to defend against actions of microorganisms such as bacteria, fungi, and yeast.

As used herein, the term "Gram-positive bacteria" means bacteria which, as a result of staining with crystal violet, appear to be purple-colored by being stained with crystal violet. About 80% to 90% of cell walls of the Gram-positive bacteria are composed of a substance called peptidoglycan. The peptidoglycan forms a thick layer to maintain size and shape of the cell walls, and serves to make the cell walls hard.

The Gram-positive bacteria may be, but are not limited to, bacteria of *Staphylococcus* sp., *Bacillus* sp., *Streptococcus* sp., or *Enterococcus* sp.

Specifically, the Gram-positive bacteria may be *Staphylococcus aureus*, methicillin-resistant *Staphylococcus aureus* (MRSA), quinolone-resistant *Staphylococcus aureus* (QRSA), vancomycin resistant enterococcus (VRE), vancomycin intermediate-resistant *Staphylococcus aureus* (VISA), *Bacillus subtilis*, *Bacillus cereus*, *Streptococcus pneumoniae*, *Enterococcus faecalis*, or *Staphylococcus epidermidis*.

As used herein, the term "Gram-negative bacteria" means bacteria which, as a result of staining with crystal violet, are not stained with crystal violet and are discolored by ethanol washing, thereby becoming violet-colored. Gram-negative bacteria have relatively thin cell walls (10 nm) and have lipopolysaccharides outside the cell walls.

The Gram-negative bacteria may be bacteria of *Salmonella* sp., *Acinetobacter* sp., *Escherichia* sp., *Pseudomonas* sp., or *Klebsiella* sp. Specifically, the Gram-negative bacteria may be *Salmonella typhimurium, Acinetobacter calcoaceticus, E. coli, Pseudomonas aeruginosa*, or *Klebsiella aerogenes*.

The antimicrobial composition of the present invention may be formulated in the form of oral preparations such as powders, granules, tablets, capsules, suspensions, emulsions, syrups, and aerosols, external preparations, suppositories, or sterilized injection solutions according to respective conventional methods, and used. Specifically, preparation thereof can be made using diluents or excipients such as fillers, extenders, binders, wetting agents, disintegrants, and surfactants which are commonly used in a case of being formulated.

Solid preparations for oral administration include, but are not limited to, tablets, pills, powders, granules, capsules, and the like. Such solid preparations can be prepared by mixing the compound of the above Formula 1, 2, 3, 4, or 5 with one or more excipients, for example, starch, calcium carbonate, sucrose, lactose, and gelatin. In addition to simple excipients, lubricants such as magnesium stearate and talc may also be used.

Liquid preparations for oral administration include, but are not limited to, suspensions, solutions, emulsions, syrups, and the like. The liquid preparations can be prepared by adding various excipients such as wetting agents, sweeteners, fragrances, and preservatives, in addition to water and liquid paraffin which are commonly used simple diluents.

Preparations for parenteral administration include sterile aqueous solutions, non-aqueous solvents, suspensions, emulsions, lyophilized preparations, and suppositories. For the non-aqueous solvents and the suspensions, propylene glycol, polyethylene glycol, vegetable oil such as olive oil, injectable ester such as ethyl oleate, and the like can be used. As bases of the suppositories, Witepsol, macrogol, Tween 61, cacao fat, laurin fat, glycerogelatin, and the like can be used.

In addition, the present invention provides an antimicrobial quasi-drug composition, comprising the peptoid of the present invention as an active ingredient. The antimicrobial quasi-drug composition is intended to prevent or ameliorate infectious diseases caused by pathogenic microorganisms or resistant bacteria.

The quasi-drug composition of the present invention may be used in combination with other quasi-drugs or quasi-drug ingredients, and may be suitably used according to a conventional method. A mixing amount of the active ingredient can be suitably determined depending on an intended use (prevention, health, or therapeutic treatment). The quasi-drug composition may be, but are not limited to, disinfectants, shower foams, mouthwash, wet tissues, detergent soaps, handwash, humidifier fillers, masks, ointments, or filter fillers.

In addition, the present invention provides a pharmaceutical composition for preventing or treating a bacterial infection, comprising the peptoid of the present invention as an active ingredient.

The bacterial infection may be any one selected from the group consisting of cholera, dysentery, pertussis, typhoid fever, laryngeal diphtheria, gland pest, pulmonary pest, scarlet fever, septicemia, pyoderma, pulmonary tuberculosis, joint tuberculosis, renal tuberculosis, tuberculous meningitis, enteritis, and food poisoning.

In addition, the pharmaceutical composition may further comprise a pharmaceutically acceptable carrier. As used herein, the term "pharmaceutically acceptable carrier" refers to a pharmaceutically acceptable material, composition, or vehicle, such as a liquid or solid filler, a diluent, an excipient, a solvent, or an encapsulation material, which is involved in delivery or transport of any composition or ingredient of interest from one organ or part of the body to another organ or part of the body. For administration, the composition of the present invention may further comprise a pharmaceutically acceptable carrier, excipient, or diluent, in addition to the above-mentioned active ingredient.

Examples of the carrier, the excipient, and the diluent may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyhydroxybenzoate, propylhydroxybenzoate, talc, magnesium stearate, and mineral oil.

As used herein, the term "prevention" means any action which suppresses infectious diseases caused by the pathogenic microorganisms or resistant bacteria, or delays development thereof, by administration of the composition.

In addition, as used herein, the term "treatment" means any action which improves or favorably alters symptoms of infectious diseases caused by the pathogenic microorganisms or resistant bacteria by administration of the composition.

The pharmaceutical composition may be administered orally or parenterally (for example, applied intravenously, subcutaneously, intraperitoneally, or topically) depending on an intended method. A dose of the pharmaceutical composition varies depending on the patient's condition and body weight, severity of disease, drug form, route of administration, and duration, and can be suitably chosen by those skilled in the art. If necessary, the pharmaceutical composition may be administered once a day or in several divided doses a day.

For prevention or treatment of bacterial infections, the pharmaceutical composition may be used alone, or in combination with methods in which surgery, hormone therapy, drug therapy, and biological response modifiers are used.

The present invention also provides a method for preventing or treating a bacterial infection, comprising administering to a subject in need thereof the peptoid having any one formula selected from the following Formulae 1 to 5:

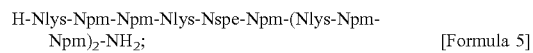

H-Nlys-Npm-Npm-Nlys-Nspe-Npm-(Nlys-Npm-Npm)$_2$-NH$_2$;  [Formula 5]

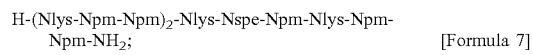

H-(Nlys-Npm-Npm)$_2$-Nlys-Nspe-Npm-Nlys-Npm-Npm-NH$_2$;  [Formula 7]

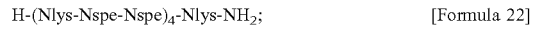

H-(Nlys-Nspe-Nspe)$_4$-Nlys-NH$_2$;  [Formula 22]

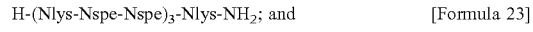

H-(Nlys-Nspe-Nspe)$_3$-Nlys-NH$_2$; and  [Formula 23]

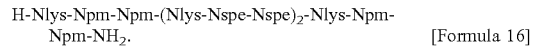

H-Nlys-Npm-Npm-(Nlys-Nspe-Nspe)$_2$-Nlys-Npm-Npm-NH$_2$.  [Formula 16]

Hereinafter, the present invention will be described in more detail with reference to the following examples. However, the following examples are merely to illustrate the present invention, and the scope of the present invention is not limited only thereto.

I. Identification of changes in activity of peptoids having altered degree of folding in helical structure Production Example 1. Preparation of peptoids having altered degree of folding in helical structure Peptoids were synthesized by manual synthesis according to a solid-phase submonomer protocol on resin beads and by heating using microwave. The heating using microwave was performed using the CEM MARS multimodal microwave reactor (CEM Corporation, Matthews, NC, USA).

C-terminal amide peptoids were constructed using the Fmoc-Rink amide MBHA resin (0.59 mmol/g, Novabiochem, San Diego, CA, USA) as resin beads. All heating reactions using microwave were carried out at atmospheric pressure. For a reaction scale, 0.25 mmol of resin beads are typically used (0.42 g of resin).

In order to cause Fmoc removal reaction to occur in the resin, the Fmoc-Rink amide resin was treated at 80° C. (microwave, 600 W max power) for 4 minutes using 5 mL of dimethylformamide (DMF) to which 20% (v/v) piperidine was added. Thereafter, the resin beads were washed with dichloromethane (DCM), DMF, and methanol (MeOH). The procedure was repeated twice.

For bromoacetylation, bromoacetic acid (4.18 mL, 1.2 M solution in DMF, 5 mmol) and N,N'-diisopropylcarbodiimide (DIC) (0.78 mL, 5 mmol) were added. The reaction solution was subjected to stirring and irradiation at 35° C. (microwave, 400 W 15% power) for 1 minute and 30 seconds.

For displacement reaction, 3.75 mL of (S)-N-(1-phenylethyl)glycine (Nspe), 5 mL of benzyl amine (Npm), or 5 mL of mono-Boc protected 1,4-diaminobutane (Nlys(Boc)) was used as primary amine. For displacement order of the primary amines, displacement was made according to the Formulae in Table 2 below.

TABLE 2

| NO. | Formula | Number of Nspe |
|---|---|---|
| 1 | H-(Nlys-Nspe-Nspe)$_4$-NH$_2$ | 8 |
| 2 | H-(Nlys-Npm-Npm)$_4$-NH$_2$ | 0 |
| 3 | H-Nlys-Nspe-Npm-(Nlys-Npm-Npm)$_3$-NH$_2$ | 1 |
| 4 | H-Nlys-Npm-Nspe-(Nlys-Npm-Npm)$_3$-NH$_2$ | 1 |
| 5 | H-Nlys-Npm-Npm-Nlys-Nspe-Npm-(Nlys-Npm-Npm)$_2$-NH$_2$ | 1 |
| 6 | H-Nlys-Npm-Npm-Nlys-Npm-Nspe-(Nlys-Npm-Npm)$_2$-NH$_2$ | 1 |
| 7 | H-(Nlys-Npm-Npm)$_2$-Nlys-Nspe-Npm-Nlys-Npm-Npm-NH$_2$ | 1 |
| 8 | H-(Nlys-Npm-Npm)$_2$-Nlys-Npm-Nspe-Nlys-Npm-Npm-NH$_2$ | 1 |
| 9 | H-(Nlys-Npm-Npm)$_3$-Nlys-Nspe-Npm-NH$_2$ | 1 |
| 10 | H-(Nlys-Npm-Npm)$_3$-Nlys-Npm-Nspe-NH$_2$ | 1 |
| 11 | H-Nlys-Nspe-Nspe-(Nlys-Npm-Npm)$_2$-Nlys-Nspe-Nspe-NH$_2$ | 4 |
| 12 | H-Nlys-Nspe-Npm-(Nlys-Npm-Npm)$_2$-Nlys-Npm-Nspe-NH$_2$ | 2 |
| 13 | H-Nlys-Nspe-Nspe-(Nlys-Npm-Npm)$_2$-Nlys-Npm-Nspe-NH$_2$ | 3 |
| 14 | H-Nlys-Nspe-Npm-(Nlys-Npm-Npm)$_2$-Nlys-Nspe-Nspe-NH$_2$ | 3 |
| 15 | H-Nlys-Npm-Npm-Nlys-Npm-Nspe-Nlys-Nspe-Nspe-Nlys-Npm-Npm-NH$_2$ | 3 |
| 16 | H-Nlys-Npm-Npm-(Nlys-Nspe-Nspe)$_2$-Nlys-Npm-Npm-NH$_2$ | 4 |
| 17 | H-Nlys-Nspe-Nspe-(Nlys-Npm-Npm)$_3$-NH$_2$ | 2 |

In this case, all synthetic peptoids contained the same number of Nlys for cationic charges, and some peptoids had the same number of Nspe for monomers that lead to a helical structure. The Nspe means a solution obtained by dissolving 3.75 mmol of Nspe using N-methylpyrrolidone (NMP) as a solvent, and has a concentration of 1.0 M. The Npm means a solution obtained by dissolving 5 mmol of Npm using NMP as a solvent, and has a concentration of 1.0 M. The Nlys(Boc) means a solution obtained by dissolving 5 mmol of Nlys(Boc) using NMP as a solvent, and has a concentration of 1.0 M.

The mixture was subjected to stirring and irradiation at 95° C. (microwave, 400 W 75% power) for 3 minutes and 30 seconds. Between each step, a step of washing the resin thoroughly with DMF, DCM, and MeOH was carried out. Separation of the peptoids from the resin was carried out with a separating solution (TFA:DCM:triisopropylsilane = 95:2.5:2.5) at room temperature for 30 minutes.

The peptoids which underwent the separation step and have altered degree of folding in helical structure are shown in Table 3 below. In Table 3 below, Peptoid NOS. 1 and 2 are known peptoids and were synthesized for the purpose of making a comparison with other novel peptoids in terms of antimicrobial activity and cytotoxicity.

TABLE 3

| NO. | Structural formula |
|---|---|
| 1 | (chemical structure) |

TABLE 3-continued

| NO. | Structural formula |
|---|---|
| 2 | |
| 3 | |
| 4 | |
| 5 | |
| 6 | |

TABLE 3-continued
| NO. | Structural formula |
|---|---|
| 7 | 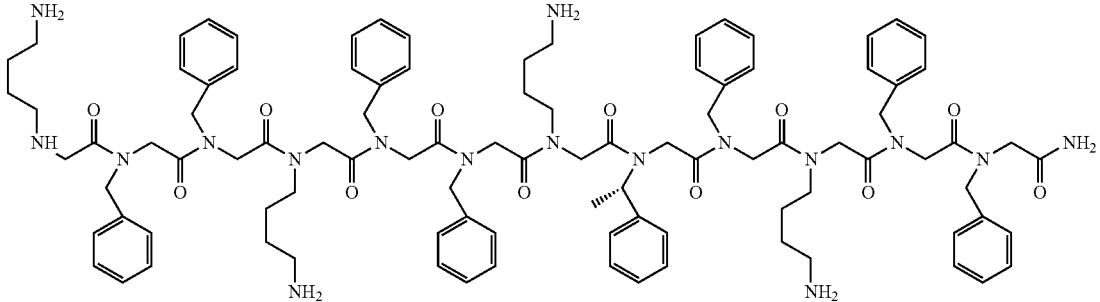 [SMILES: C[C@@H](c1ccccc1)N(CC(=O)N(CC(=O)N(CCCCN)CC(=O)N(CC(=O)N(CC(N)=O)Cc1ccccc1)Cc1ccccc1)Cc1ccccc1)C(=O)CN(CCCCN)C(=O)CN(Cc1ccccc1)C(=O)CN(Cc1ccccc1)C(=O)CN(CCCCN)C(=O)CN(Cc1ccccc1)C(=O)CN(Cc1ccccc1)C(=O)CNCCCCN] |
| 8 | 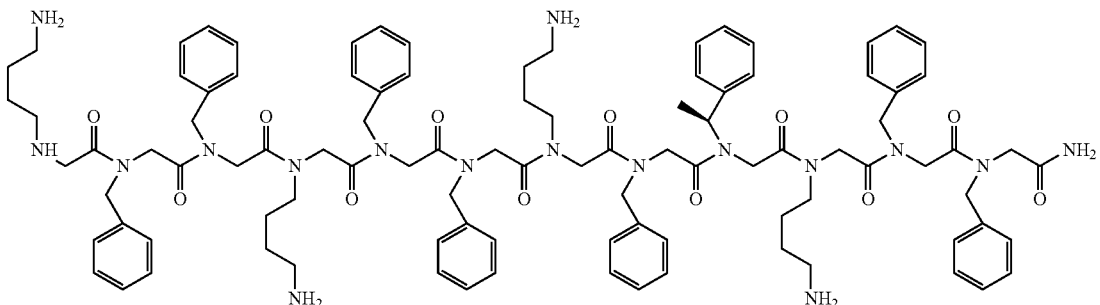 [SMILES: C[C@@H](c1ccccc1)N(CC(=O)N(CCCCN)CC(=O)N(CC(=O)N(CC(N)=O)Cc1ccccc1)Cc1ccccc1)C(=O)CN(Cc1ccccc1)C(=O)CN(CCCCN)C(=O)CN(Cc1ccccc1)C(=O)CN(Cc1ccccc1)C(=O)CN(CCCCN)C(=O)CN(Cc1ccccc1)C(=O)CN(Cc1ccccc1)C(=O)CNCCCCN] |
| 9 | 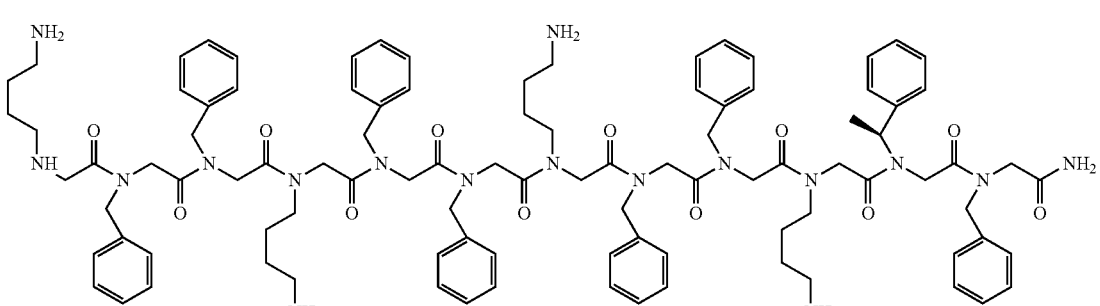 |
| 10 | 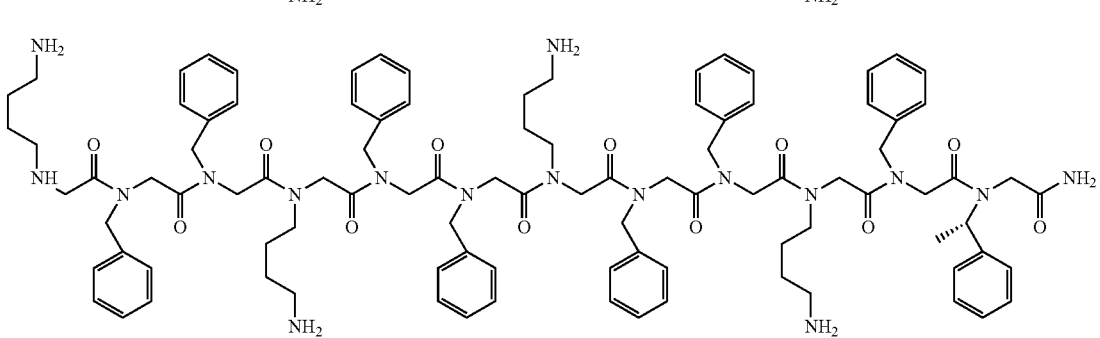 |
| 11 | 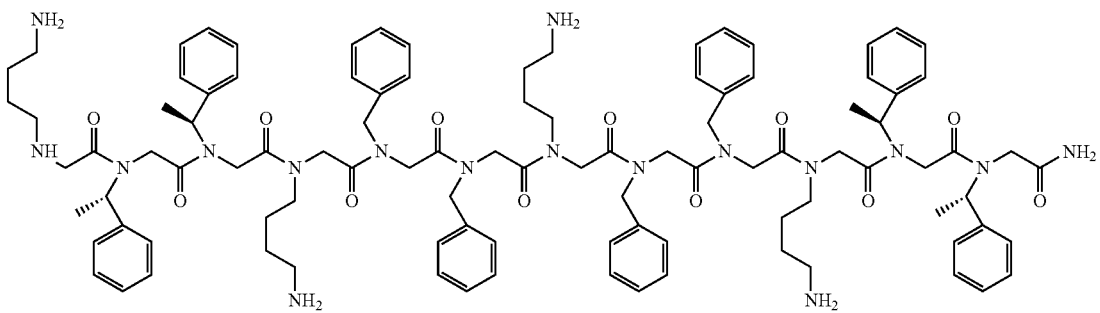 [SMILES: C[C@@H](c1ccccc1)N(CC(N)=O)C(=O)CN(C(=O)CN(CCCCN)C(=O)CN(Cc1ccccc1)C(=O)CN(Cc1ccccc1)C(=O)CN(CCCCN)C(=O)CN(Cc1ccccc1)C(=O)CN(Cc1ccccc1)C(=O)CN(CCCCN)C(=O)CN(C(=O)CN(C(=O)CNCCCCN)[C@@H](C)c1ccccc1)[C@@H](C)c1ccccc1)[C@@H](C)c1ccccc1] |

TABLE 3-continued

| NO. | Structural formula |
|-----|--------------------|
| 12 | |
| 13 | |
| 14 | |
| 15 | |
| 16 | |

TABLE 3-continued

| NO. | Structural formula |
|---|---|
| 17 | (structure) |

The synthesized peptoids were purified and analyzed using HPLC and LC-MS. As a result, the synthesized peptoids showed considerably similar residence times in the HPLC analysis. This identified that the synthesized peptoids have similar hydrophobicity (FIGS. 3 to 19). In addition, the HPLC and LC-MS analysis results for the synthesized peptoids are shown in Table 4 below.

TABLE 4

| NO. | Molecular weight (MW, Da) | HPLC elution (% ACN) | Net charge |
|---|---|---|---|
| 1 | 1819.36 | 54.4 | +4 |
| 2 | 1707.15 | 50.7 | +4 |
| 3 | 1721.17 | 51.1 | +4 |
| 4 | 1721.17 | 49.8 | +4 |
| 5 | 1721.17 | 50.3 | +4 |
| 6 | 1721.17 | 50.0 | +4 |
| 7 | 1721.17 | 51.5 | +4 |
| 8 | 1721.17 | 51.2 | +4 |
| 9 | 1721.17 | 51.7 | +4 |
| 10 | 1721.17 | 51.4 | +4 |
| 11 | 1763.26 | 52.2 | +4 |
| 12 | 1735.20 | 51.5 | +4 |
| 13 | 1749.23 | 51.5 | +4 |
| 14 | 1749.23 | 52.3 | +4 |
| 15 | 1749.23 | 52.1 | +4 |
| 16 | 1763.26 | 52.7 | +4 |
| 17 | 1735.20 | 51.0 | +4 |

Experimental Example 1

Identification of Antimicrobial Activity of Peptoids

In order to measure antimicrobial activity of the peptoids, Gram-positive *S. aureus* strain KCTC1621, or Gram-negative *E. coli* strain ATCC25922 was treated with the peptoids prepared in Preparation Example 1, and minimum inhibitory concentrations were measured. Peptoid NOS. 1 and 2 are already known peptoids and were used for the purpose of making a comparison with novel peptoids in terms of antimicrobial activity.

Specifically, *S. aureus* strain KCTC1621 or *E. coli* strain ATCC25922 was inoculated into Mueller Hinton Broth (MHB2) liquid medium on which cations were adjusted, cultured at a temperature of 37° C. for 18 hours, and then subcultured for 4 hours. Thereafter, the strains were diluted with MHB2 liquid medium containing 0.2% bovine serum albumin and 0.01% acetic acid so that each bacterial number was $2\times10^5$ colony-forming units (CFU) per 1 mL, and dispensed into 96-well microtiter plates at 100 μL each. A peptoid stock which is 40-fold more concentrated than a concentration to be tested was added to each well at 2.5 μL or lower so that the peptoid stock was 2-fold serially diluted using sterile water. Thereafter, the plates were incubated at a temperature of 37° C. for 18 hours.

Thereafter, absorbance was measured at a wavelength of 600 nm using a microplate reader (Bio-Rad). The lowest peptoid concentration that completely suppresses growth of microorganisms was measured by a minimum inhibitory concentration (MIC) and a minimum bactericidal concentration (MBC), and the measurement results are shown in Table 5 below. Each of the MIC values was calculated as an average value of numerical values obtained through three independent experiments.

TABLE 5

| | MIC (μM) | | MBC (μM) | |
|---|---|---|---|---|
| NO. | S. aureus | E. coli | S. aureus | E. coli |
| 1 | <0.8 | 3.1 | 1.6 | 3.1 |
| 2 | 3.1 | 25 | 6.3 | >25 |
| 3 | 3.1 | 25 | 3.1 | 25 |
| 4 | 3.1 | 12.5 | 3.1 | 25 |
| 5 | 3.1 | 12.5 | 3.1 | 12.5 |
| 6 | 3.1 | 12.5 | 3.1 | 25 |
| 7 | 3.1 | 12.5 | 3.1 | 25 |
| 8 | 3.1 | 12.5 | 3.1 | 25 |
| 9 | 3.1 | 12.5 | 3.1 | 25 |
| 10 | 3.1 | 12.5 | 3.1 | 25 |
| 11 | 3.1 | 12.5 | 6.3 | 25 |
| 12 | 3.1 | 12.5 | 3.1 | 25 |
| 13 | 3.1 | 25 | 6.3 | 25 |
| 14 | 1.6 | 12.5 | 1.6 | 12.5 |
| 15 | 3.1 | 12.5 | 3.1 | 25 |
| 16 | 1.6 | 6.3 | 3.1 | 6.3 |
| 17 | 3.1 | 25 | 3.1 | 25 |

As a result, overall, the minimum inhibitory concentration values were exhibited at low μM concentrations for *S. aureus* strain KCTC1621, and the lowest minimum inhibitory concentration value was measured for Peptoid NO. 1. In addition, for Gram-negative *E. coli* strain ATCC25922, Peptoid NO. 1 also exhibited the lowest minimum inhibitory concentration value, and the next lowest minimum inhibitory concentration value was measured for Peptoid NO. 16. Peptoid NO. 16 was identified which has high activity against Gram-negative bacteria for which there is lack of effective antibiotics as compared with Gram-positive bacteria. Like Peptoid NO. 1, it was shown that Peptoid NO. 16 also has the same value for the minimum inhibitory concentration and minimum bactericidal concentration.

Experimental Example 2

Identification of Hemolytic Activity of Peptoids

In order to identify, through red blood cell hemolytic activity in mice, whether the peptoids synthesized in Preparation Example 1 are cytotoxic, red blood cells isolated from 10 mL of mouse blood were washed three times with phosphate-buffered saline (PBS, mixed solution of 35 mM phosphate buffer/150 mM NaCl, pH 7.4), and then centrifuged at a centrifugal force of 1,000 ×g for 10 minutes. A 10% (v/v) red blood cell solution diluted with PBS was dispensed into a 96-well microtiter plate at 150 μL each, and then a peptide solution was added at 50 μL each. Thereafter, the 96-well microtiter plate was incubated at a temperature of 37° C. for 1 hour.

The incubated 96-well microtiter plate was centrifuged at a centrifugal force of 1,000×g for 5 minutes. Thereafter, supernatant was taken at 100 μL each and transferred to a new 96-well microtiter plate. Then, absorbance at a wavelength of 540 nm was measured (Table 6).

In this case, a value obtained in a case of being treated with 0.1% (v/v) Triton X-100 was set as 100% hemolysis, and hemolytic activity (degree of cell destruction) of the peptoids was calculated using the following Equation 1. In the Equation 1, A is absorbance of the peptoid solution at a wavelength of 540 nm, B is absorbance of 0.1% Triton X-100 at a wavelength of 540 nm, and C is absorbance of the PBS solution at a wavelength of 540 nm. In this case, Peptoid NO. 1 that exhibits strong hemolytic activity was used as a control.

Degree of cell destruction (% hemolysis)=(A−C)/(B−C)×10  [Equation 1]

TABLE 6

| NO. | $HD_{10}/HD_{50}$ | $H_{max}$ (%) |
|---|---|---|
| 1 | 1.2/42.8 | 113.4 ± 2.0 |
| 2 | >200/>200 | 9.2 ± 0.4 |
| 3 | 112.7/>200 | 31.0 ± 5.3 |
| 4 | 89.6/>200 | 32.9 ± 0.5 |
| 5 | 106.5/195.0 | 52.2 |
| 6 | 101.4/185.4 | 57.0 |
| 7 | 153.9/>200 | 41.0 |
| 8 | 88.5/>200 | 30.8 |
| 9 | 54.4/>200 | 40.1 |
| 10 | 103.3/>200 | 35.2 |
| 11 | 61.6/>200 | 46.4 ± 1.7 |
| 12 | 79.7/>200 | 43.4 ± 2.7 |
| 13 | 81.7/>200 | 16.0 ± 5.1 |
| 14 | 53.9/199.6 | 51.4 ± 3.3 |
| 15 | 26.8/155.8 | 61.4 ± 4.5 |
| 16 | 53.0/>200 | 47.2 ± 2.3 |
| 17 | 120.3/>200 | 30.8 ± 2.5 |

In Table 6, $HD_{10}$ means a peptoid concentration which causes 10% hemolysis of red blood cells, and $HD_{50}$ means a peptoid concentration which causes 50% hemolysis of red blood cells. In addition, $H_{max}$ is a hemolysis rate (%) at 200 μM which is the highest peptoid concentration used in the experiment.

As a result, a high-concentration $HD_{50}$ value was measured for Peptoid NOS. 2 to 17 except Peptoid NO. 1. In addition, a high-concentration $HD_{10}$ value was measured only for Peptoid NOS. 2, 5, 7, and 17.

Experimental Example 3

Analysis of Degree of Folding in Helical Structure of Peptoids

For analysis of degree of folding in helical structure of the peptoids, the peptoids prepared in Preparation Example 1 were analyzed with the Jasco 810 circular dichroism spectropolarimeter (JASCO, Easton, Md., USA) using, as a solvent, acetonitrile, Tris buffer, or Tris buffer which contains lipid vesicles (POPE:POPG=7:3) mimicking bacterial membrane. Peptoid NOS. 1 and 2 are already known antimicrobial peptoids and were used for the purpose of making a comparison with novel peptoids in terms of difference in helical structure.

Specifically, in a case of lipid vesicles, POPE and POPG (25 mg/mL) dissolved in chloroform were mixed at a molar ratio of 7:3, and then made into a lipid film using an evaporator. Thereafter, the lipid film was dissolved in 20 mM Tris buffer and the dissolution was carried out at a temperature of 40° C. for 1 hour. The lipid suspension thus formed was subjected to ultrasonic treatment again at a temperature of 40° C. for about 30 to 45 minutes until the liquid suspension became transparent. For the finally obtained lipid vesicles, use thereof was made complete within 6 hours. A solution consisting of 5 mM lipid vesicles and 10 mM Tris buffer (pH 7.0) together with 50 μM peptoid as prepared above was used for circular dichroism spectropolarimetry.

Structural analysis of the prepared peptoids was carried out using a circular dichroism spectropolarimeter, in which a quartz cell with a path length of 1 mm or 0.2 mm was used as a container for analysis. Response time for analysis was set to 1 second, and bandwidth was set to 1.0 nm. Peptoid NOS. 1 to 17 as prepared above were measured for their initial helix structure in an acetonitrile solvent, and spectra were allowed to proceed at a temperature of 20° C. in a range of 190 nm to 260 nm and with a scanning rate of 20 nm/min The spectral results were calculated as an average of three measurement values. These results were expressed as per-residue molar ellipticity depending on a peptoid length.

In addition, Peptoid NOS. 1, 2, and 11 to 17 were measured at a condition of 5 mM Tris buffer (pH 7.0) or 10 mM Tris buffer containing 5 mM POPE:POPG (7:3) lipid vesicles. In this case, spectra were allowed to proceed at a temperature of 20° C. in a range of 190 nm to 260 nm and with a scanning rate of 100 nm/min The spectra were allowed to proceed under a condition at a data pitch of 0.2 nm, bandwidth of 1 nm, and response time of 2 seconds. Measurements were performed 40 times, and the results were expressed as an average value thereof.

Figure 1B:
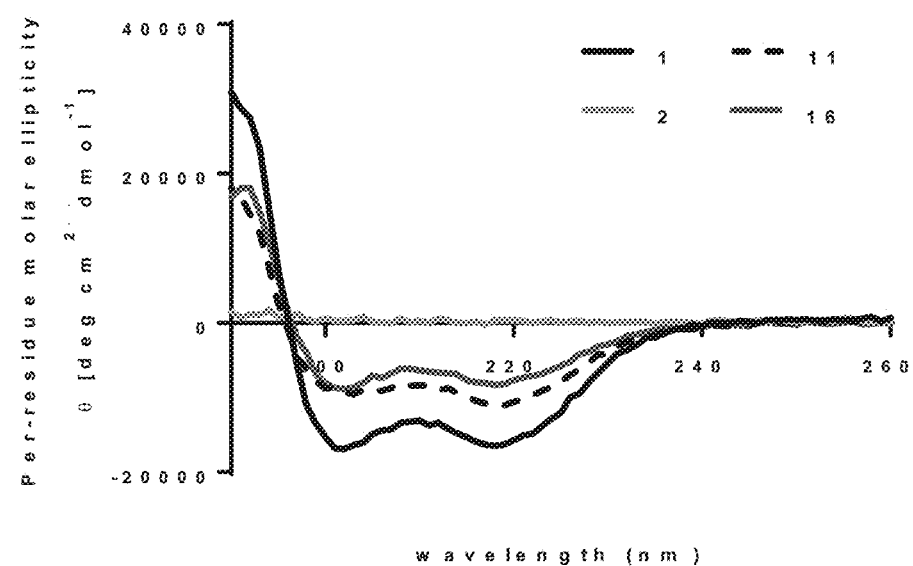
FIG. 1B is a diagram obtained by analyzing a degree of folding in helical structure of a multiple-Nspe peptoid in acetonitrile (solvent) using a circular dichroism spectropolarimeter.
Figure 1C:
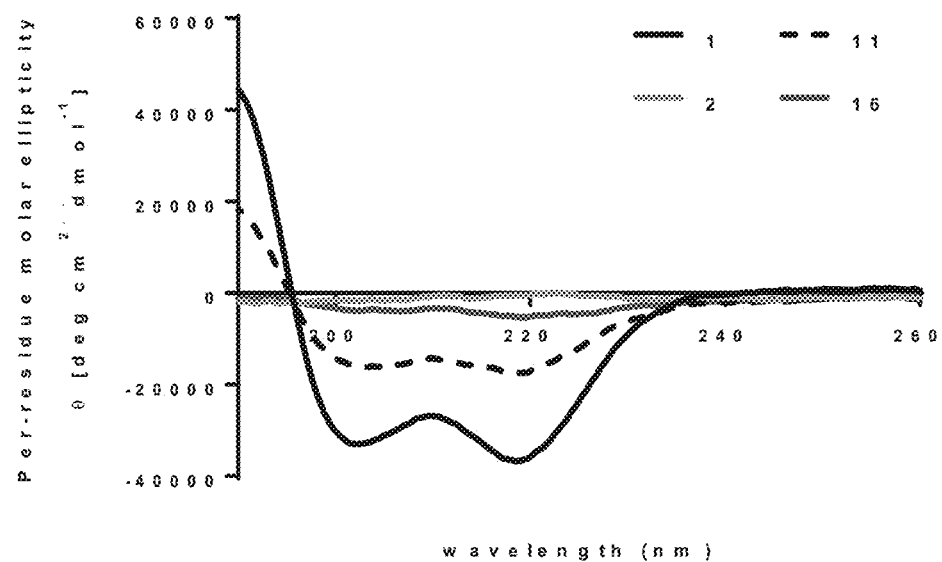
FIG. 1C is a diagram obtained by analyzing a degree of folding in helical structure of a multiple-Nspe peptoid in Tris buffer (solvent) using a circular dichroism spectropolarimeter.
Figure 1D:
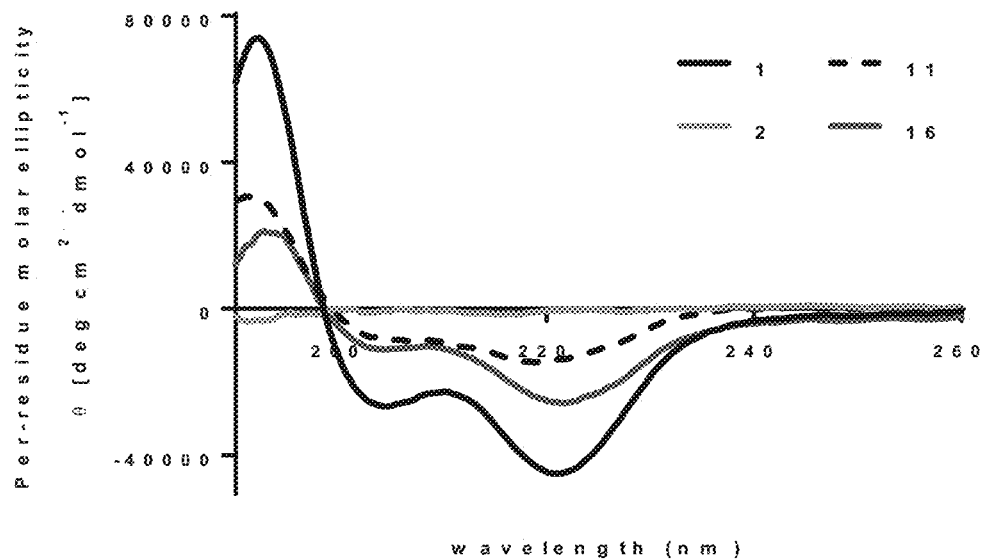
FIG. 1D is a diagram obtained by analyzing a degree of folding in helical structure of a multiple-Nspe peptoid in lipid vesicles using a circular dichroism spectropolarimeter.

As a result, it was identified through circular dichroism spectropolarimetry that the peptoids have different degrees of helical structure depending on a Nspe position. In particular, it was identified that $3^{rd}$ and $12^{th}$ positions from the N-terminus have the greatest influence on structure determination (FIG. 1A). In addition, it was identified that the peptoids containing Nspe at various numbers and positions retain their tendency in acetonitrile and Tris buffer (FIGS. 1B and 1C). On the other hand, it was identified that a helical structure of Peptoid NO. 16 is strongly formed in lipid vesicles (POPE:POPG=7:3) mimicking a membrane structure of E. coli (FIG. 1D).

From these results, it was found that interaction between the synthesized peptoids and the bacterial membrane structure varies depending on a degree of helical structure of the synthesized peptoids. Correlation results between the helical structure of the synthesized peptoids and a mimic for the *E. coli* membrane structure are shown in FIGS. 1A to 1D. It was identified that for Peptoid NO. 16 with enhanced selectivity to bacteria, a weak helical structure is formed on Tris buffer, but a helical structure is strongly formed in a case where lipid vesicles (POPE:POPG=7:3) are present.

Experimental Example 4

Identification of Antimicrobial Activity of Peptoids in Multidrug-Resistant Bacteria Minimum inhibitory concentrations of the prepared peptoids for multidrug-resistant bacteria were measured using a modified microdilution method in Difco Mueller Hinton medium, and tests were done on a panel of bacterial pathogens which have resistance and tolerance against common antibiotics.

Briefly, a peptoid concentrate, which is 10-fold more concentrated than a final concentration, was serially diluted with a medium containing 0.2% bovine serum albumin and 0.01% acetic acid. 10 μL of the 10-fold concentrated peptoid concentrate and 90 μL of Muller Hinton medium were added to each well of a 96-well polypropylene microtitre plate. Bacteria were added to the plate so that a final concentration thereof was $2 \times 10^5$ CFU/mL, and then incubated overnight at a temperature of 37° C. The minimum inhibitory concentration was defined as a concentration at which no bacterial growth is observed.

Antimicrobial activity of the peptoids against multidrug-resistant bacteria is shown in Table 7 below. In addition, in Table 5 above, Peptoid NO. 1 showed the lowest minimum inhibitory concentration for multidrug-resistant bacteria, similar to the antimicrobial activity thereof against Gram-negative *E. coli* strain ATCC25922 and Gram-positive *S. aureus* strain KCTC1621. Novel peptoids with modulated helical structure showed a minimum inhibitory concentration similar to that of Peptoid NO. 1 for Gram-positive *S. aureus* strain ATCC25923, and multidrug-resistant Gram-positive *S. epidermidis* strain (ET-024 MRSA). It was identified that the novel peptoids exhibit a relatively high minimum inhibitory concentration for multidrug-resistant Gram-negative bacteria (*P. aeruginosa* and *E. coli*) as compared with Peptoid NO. 1. For *E. coli*, the novel peptoids showed a similar tendency to the antimicrobial activity data in Table 5.

Experimental Example 5

Identification of Metabolic Stability of Antimicrobial Peptoids

In order to identify metabolic stability of the peptoids synthesized in Preparation Example 1, such peptoids were subjected to enzymatic reaction using S9 fraction which is a mixture of human liver tissue-extracted metabolic enzymes. Thereafter, for the reaction products, metabolites were quantitated using HPLC.

Specifically, Peptoid NOS. 1 and 4, and Pexiganan as a peptide control (40 μL each, 100 μM) were treated with 100 μM Tris-HCl, 3.3 mM $MgCl_2$, and 1.3 mM NADPH buffer (306 μL, pH=7.4), to prepare respective samples. The respective samples were treated with S9 fraction (2 μL, 0.1 mg/mL) and then incubated at a temperature of 37° C. When 0, 1, 4, and 24 hours had elapsed after treatment with the S9 fraction, 40 μL of each sample was taken out, and acetonitrile containing the same amount of 0.1% trifluoroacetic acid was used to stop activity of enzymes contained in the S9 fraction. Thereafter, proteins precipitated with acetonitrile were centrifuged at a condition of 1,000×g for 10 minutes at a temperature of 4° C. Then, supernatant was analyzed by HPLC to identify an amount of the remaining peptoid which had not been degraded by the enzymes in the S9 fraction.

Figure 2A:
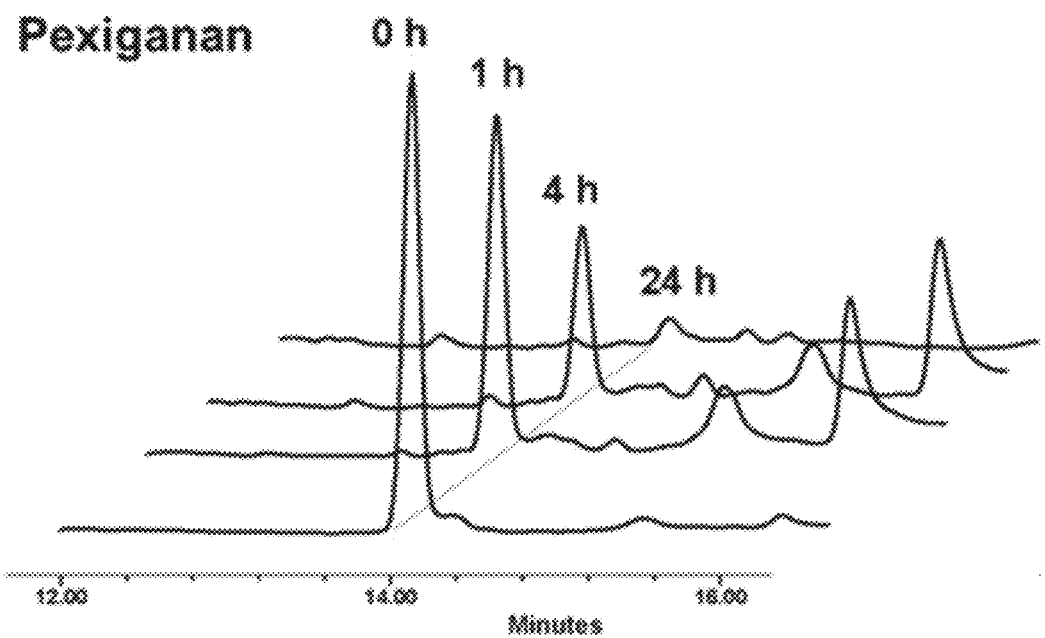
FIG. 2A is a diagram obtained by treating Pexiganan with human liver S9 fraction, and then measuring undegraded Pexiganan over time by using HPLC.
Figure 2B:
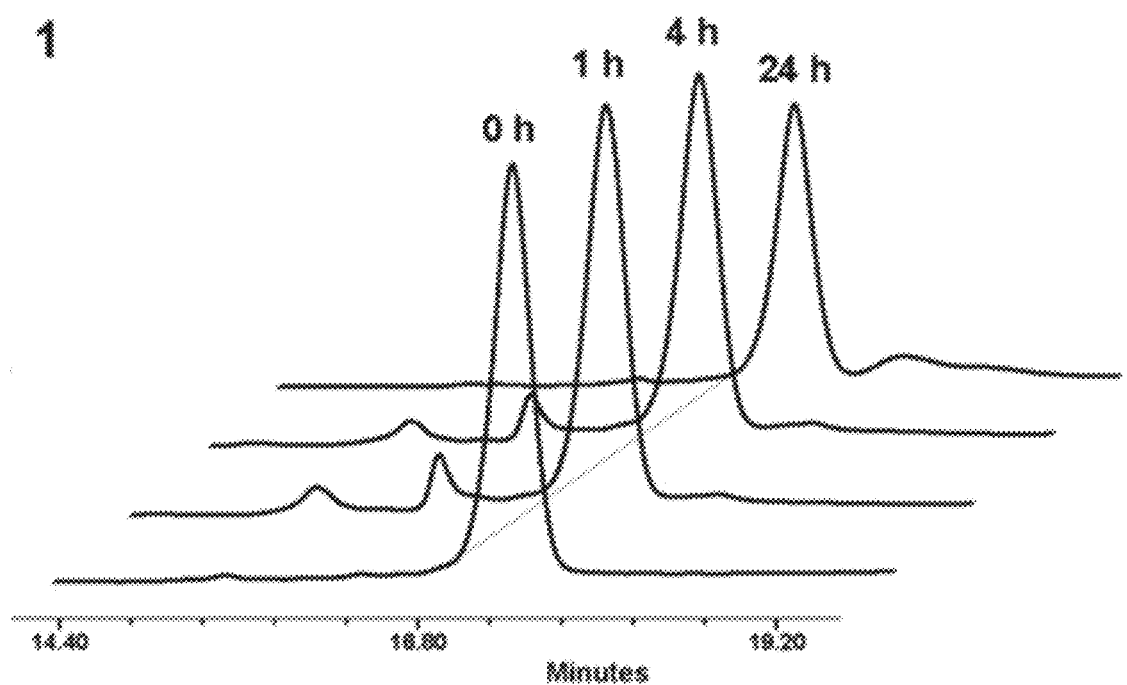
FIG. 2B is a diagram obtained by treating Peptoid NO. 1 with human liver S9 fraction, and then measuring undegraded Peptoid NO. 1 over time by using HPLC.
Figure 2C:
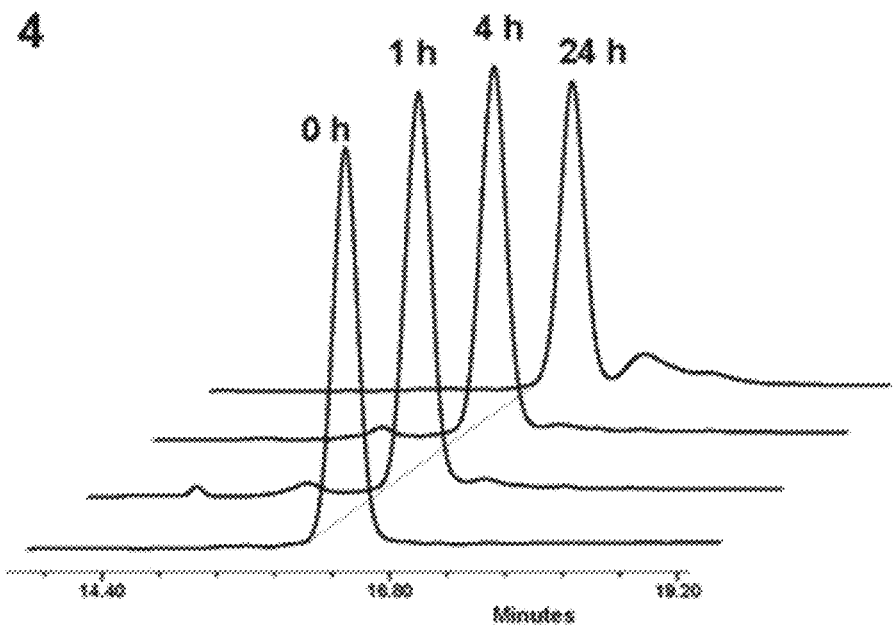
FIG. 2C is a diagram obtained by treating Peptoid NO. 4 with human liver S9 fraction, and then measuring undegraded Peptoid NO. 4 over time by using HPLC.
Figure 3:
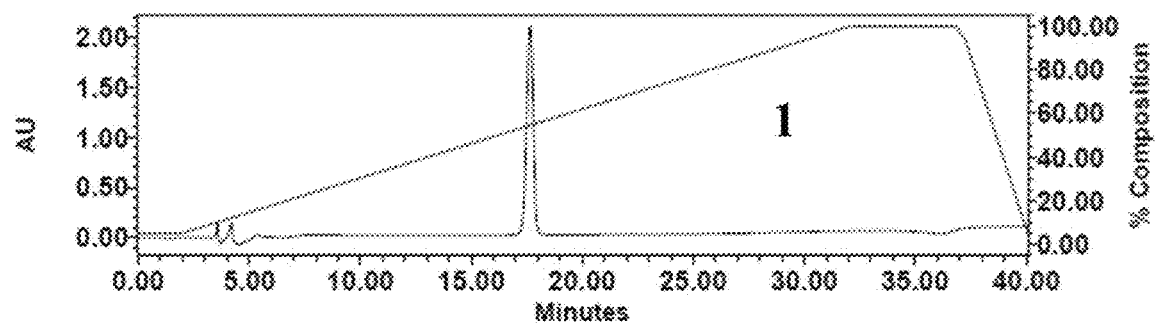
FIG. 3 is a diagram showing results of analysis for Peptoid NO. 1 purified through high-performance liquid chromatography.
Figure 4:
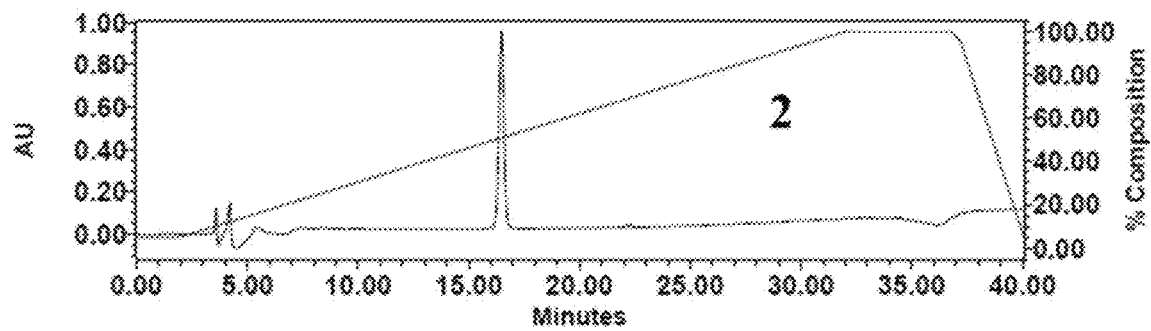
FIG. 4 is a diagram showing results of analysis for Peptoid NO. 2 purified through high-performance liquid chromatography.
Figure 5:
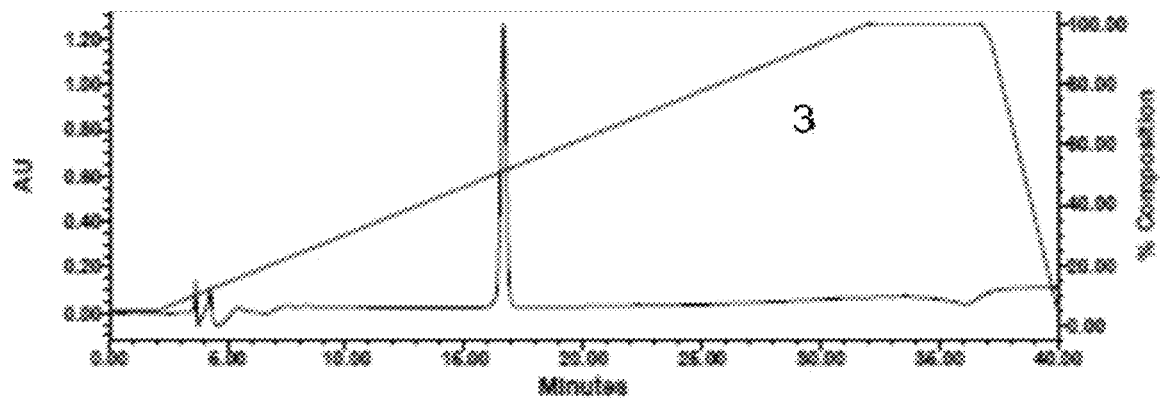
FIG. 5 is a diagram showing results of analysis for Peptoid NO. 3 purified through high-performance liquid chromatography.
Figure 6:
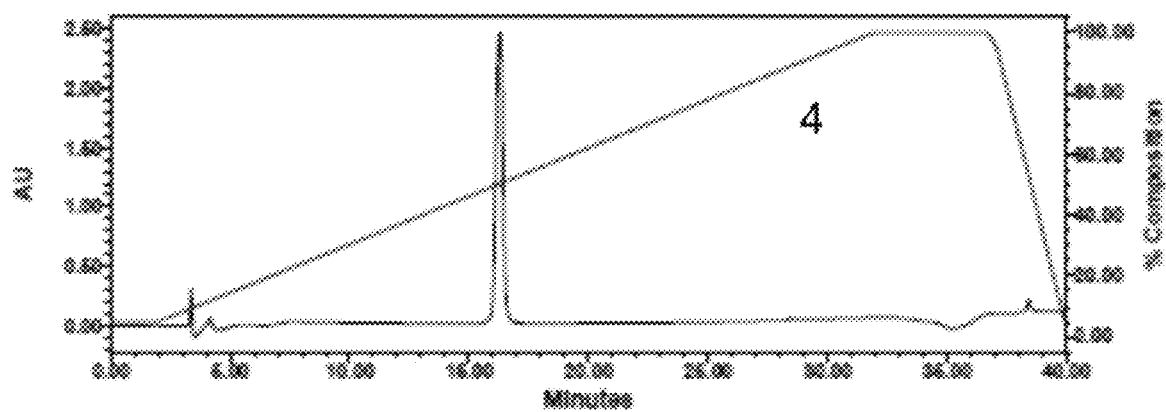
FIG. 6 is a diagram showing results of analysis for Peptoid NO. 4 purified through high-performance liquid chromatography.
Figure 7:
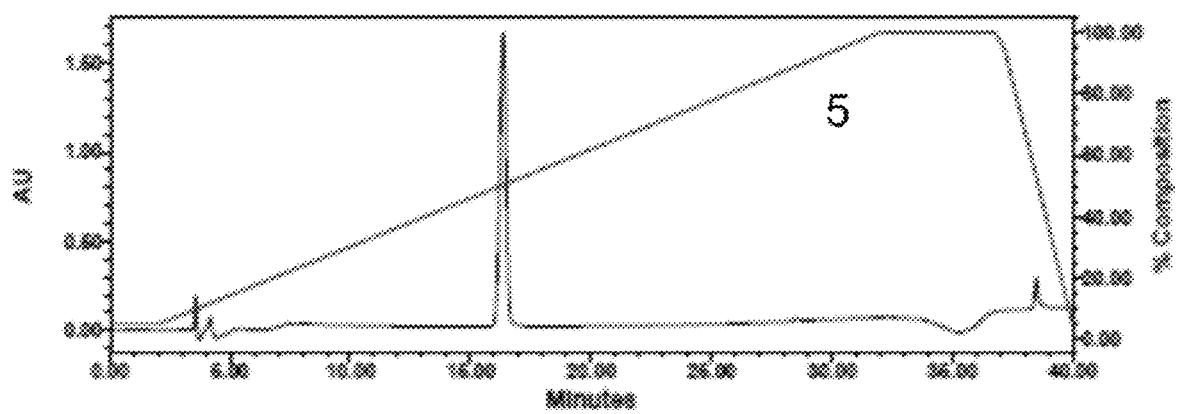
FIG. 7 is a diagram showing results of analysis for Peptoid NO. 5 purified through high-performance liquid chromatography.
Figure 8:
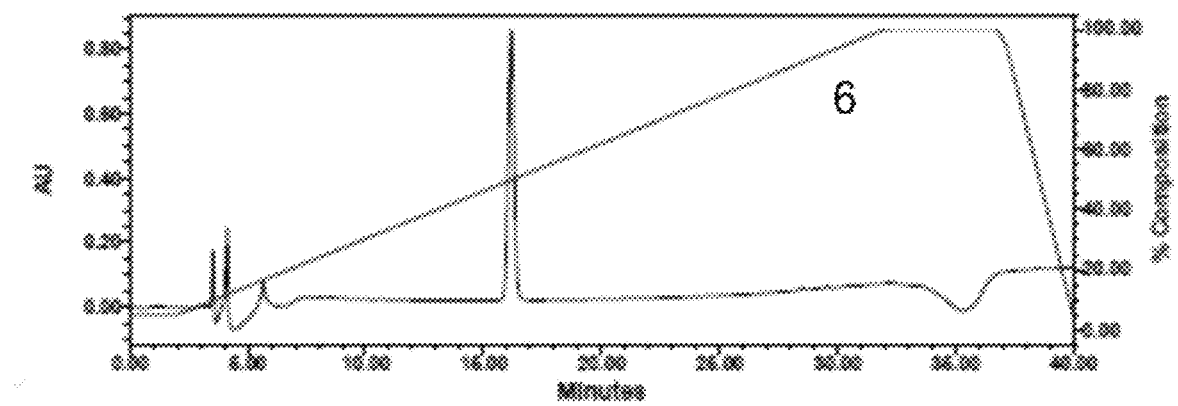
FIG. 8 is a diagram showing results of analysis for Peptoid NO. 6 purified through high-performance liquid chromatography.
Figure 9:
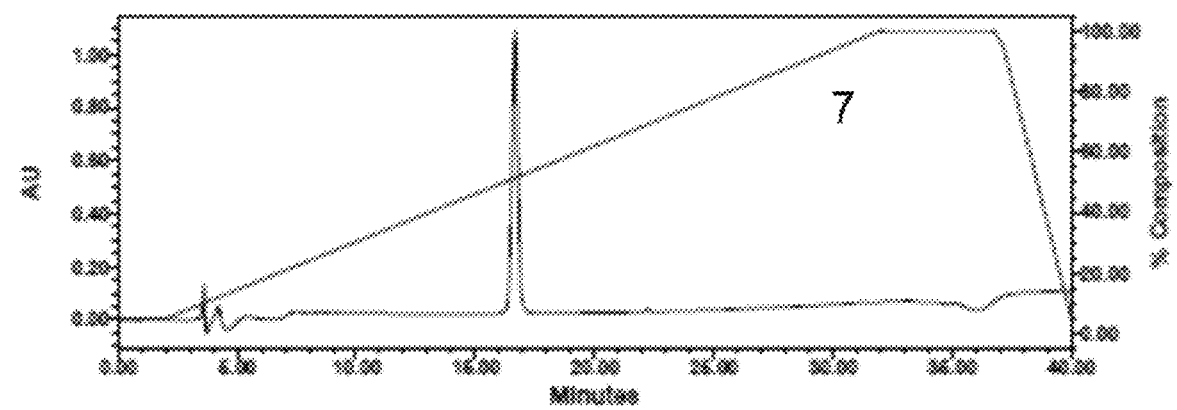
FIG. 9 is a diagram showing results of analysis for Peptoid NO. 7 purified through high-performance liquid chromatography.
Figure 10:
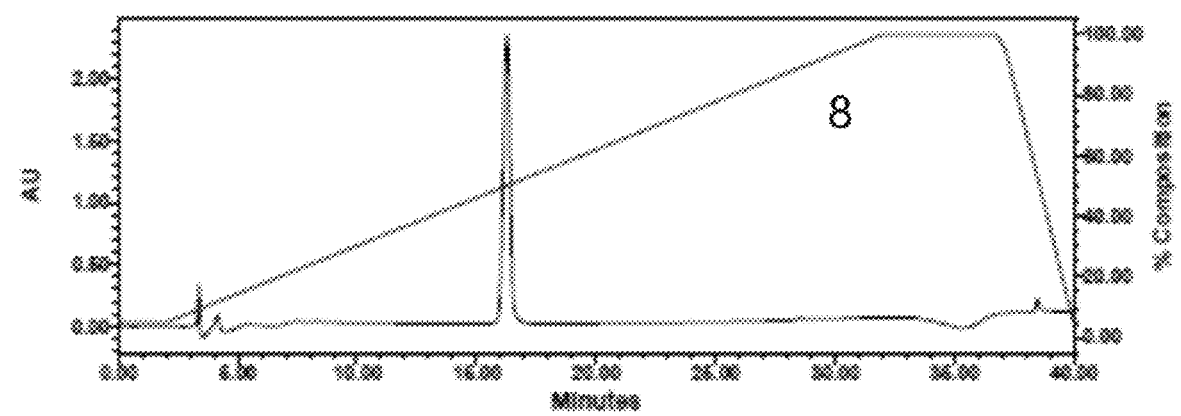
FIG. 10 is a diagram showing results of analysis for Peptoid NO. 8 purified through high-performance liquid chromatography.
Figure 11:
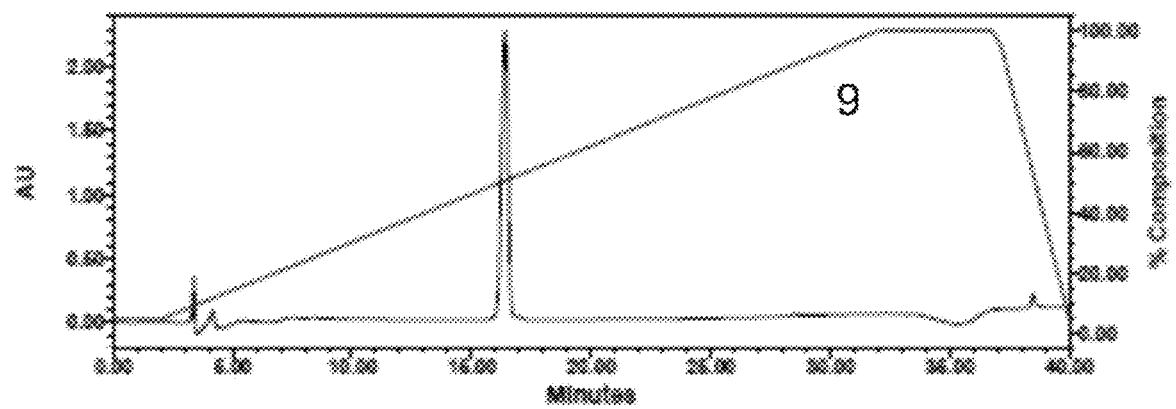
FIG. 11 is a diagram showing results of analysis for Peptoid NO. 9 purified through high-performance liquid chromatography.
Figure 12:
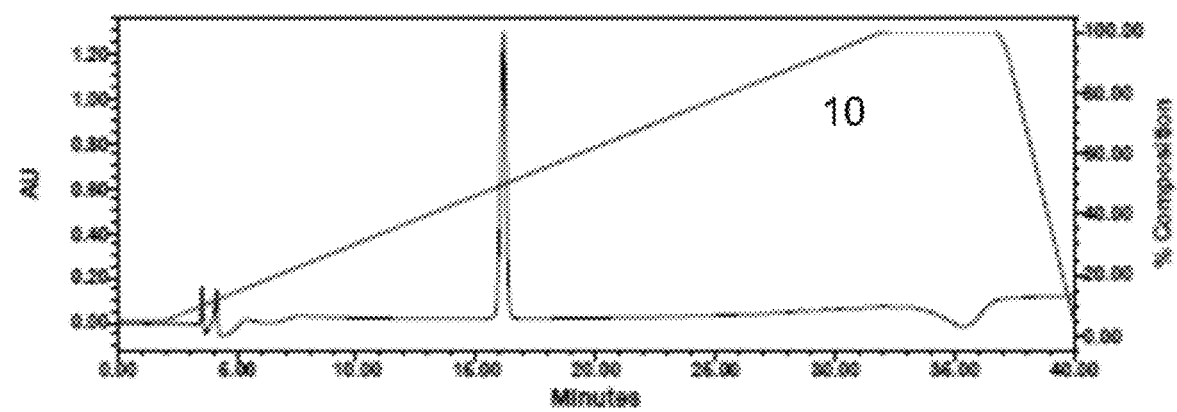
FIG. 12 is a diagram showing results of analysis for Peptoid NO. 10 purified through high-performance liquid chromatography.
Figure 13:
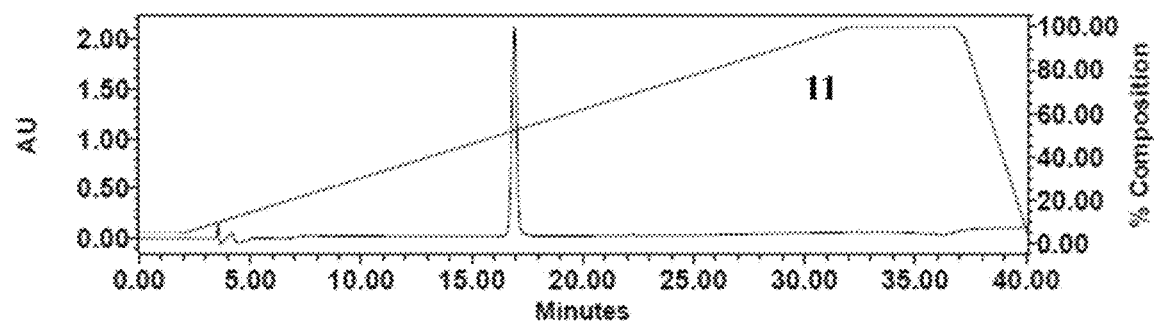
FIG. 13 is a diagram showing results of analysis for Peptoid NO. 11 purified through high-performance liquid chromatography.
Figure 14:
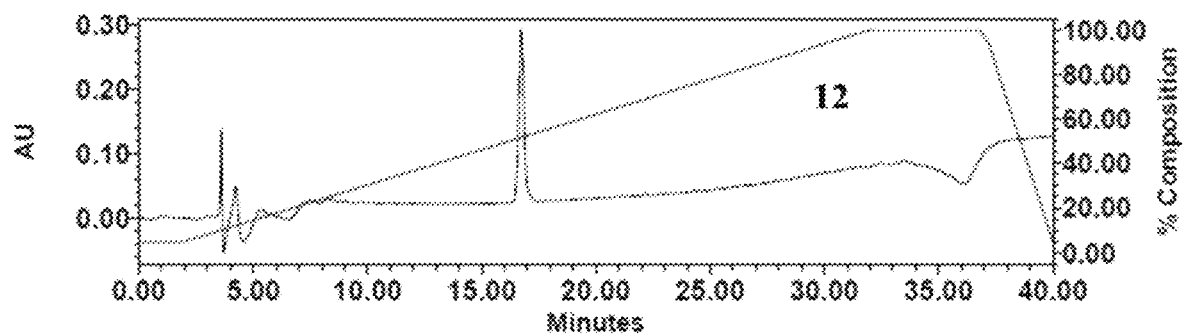
FIG. 14 is a diagram showing results of analysis for Peptoid NO. 12 purified through high-performance liquid chromatography.
Figure 15:
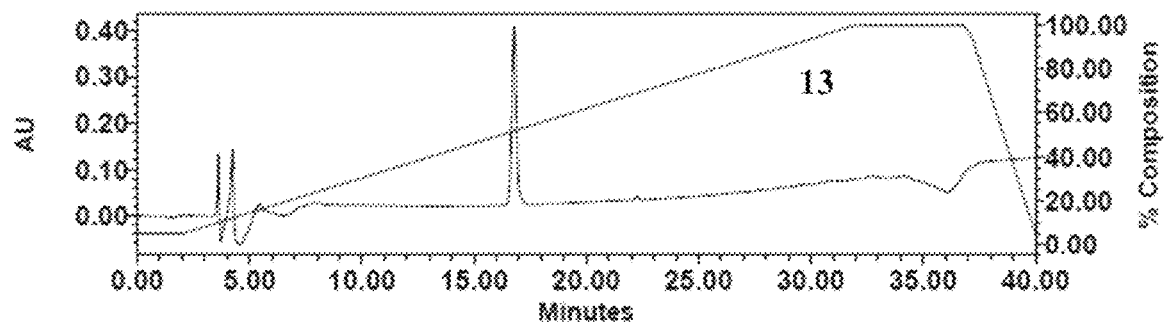
FIG. 15 is a diagram showing results of analysis for Peptoid NO. 13 purified through high-performance liquid chromatography.
Figure 16:
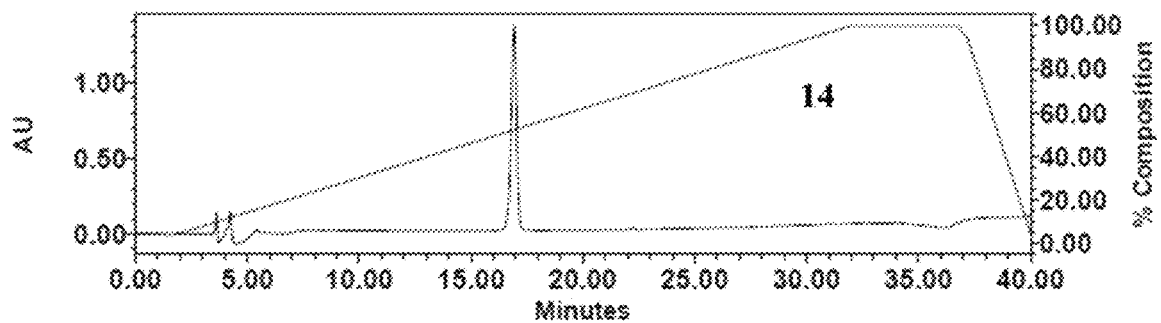
FIG. 16 is a diagram showing results of analysis for Peptoid NO. 14 purified through high-performance liquid chromatography.
Figure 17:
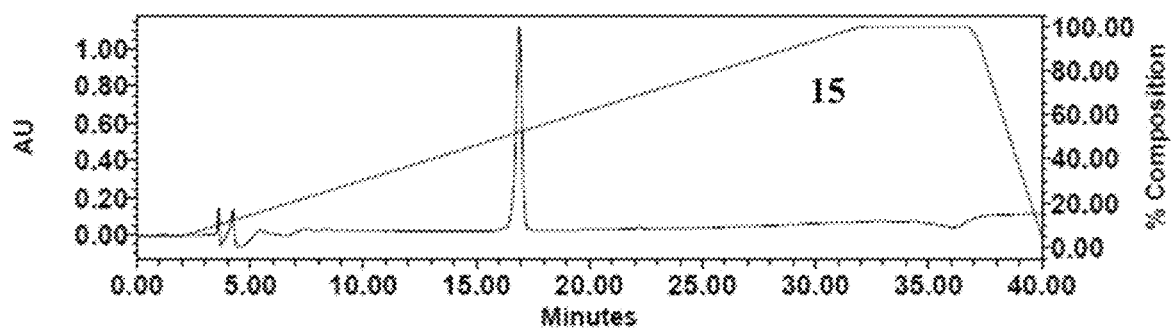
FIG. 17 is a diagram showing results of analysis for Peptoid NO. 15 purified through high-performance liquid chromatography.
Figure 18:
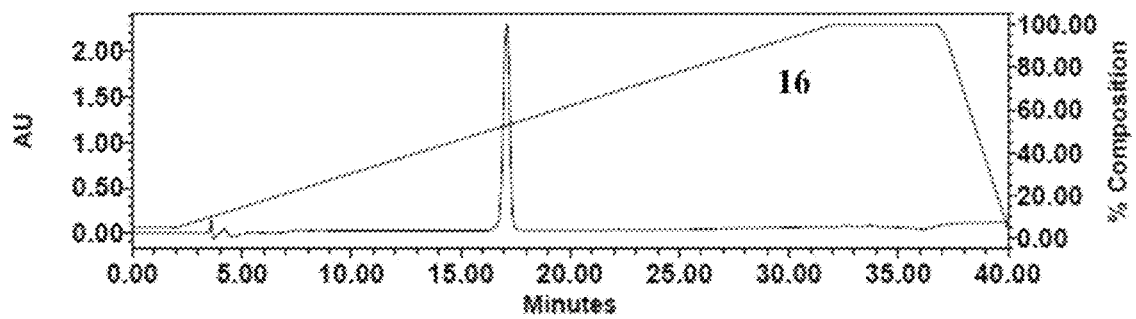
FIG. 18 is a diagram showing results of analysis for Peptoid NO. 16 purified through high-performance liquid chromatography.
Figure 19:
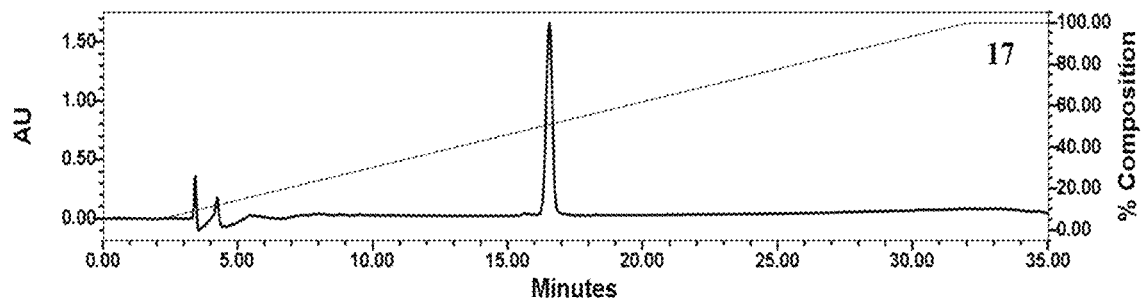
FIG. 19 is a diagram showing results of analysis for Peptoid NO. 17 purified through high-performance liquid chromatography.
Figure 20:
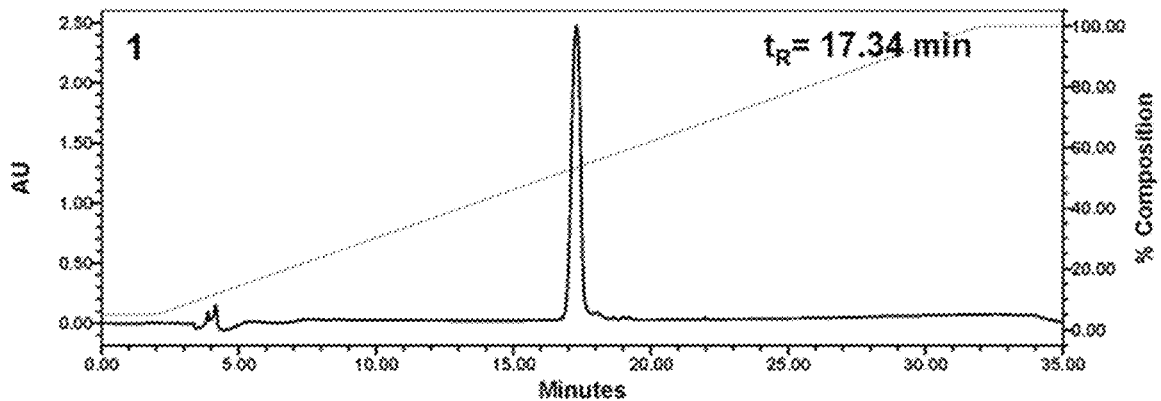
FIG. 20 is a diagram showing results of analysis for Peptoid NO. 1 purified through high-performance liquid chromatography.
Figure 21:
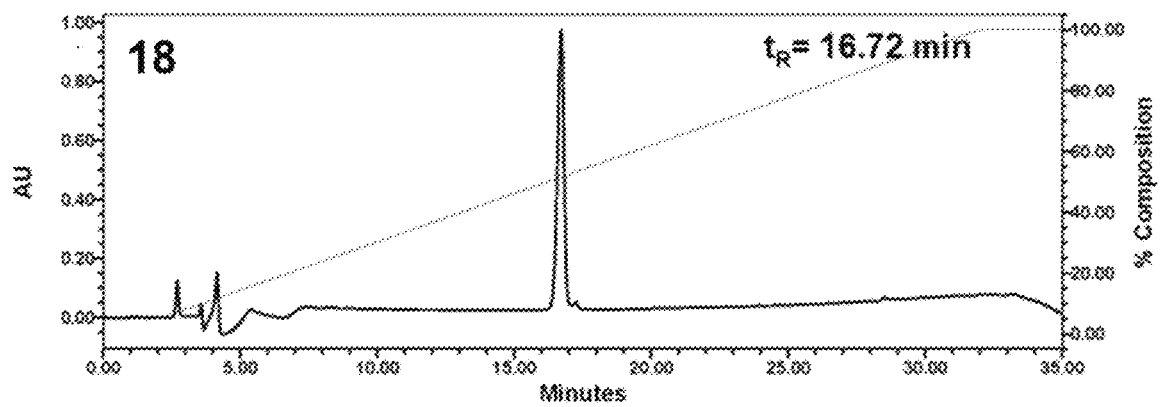
FIG. 21 is a diagram showing results of analysis for Peptoid NO. 18 purified through high-performance liquid chromatography.
Figure 22:
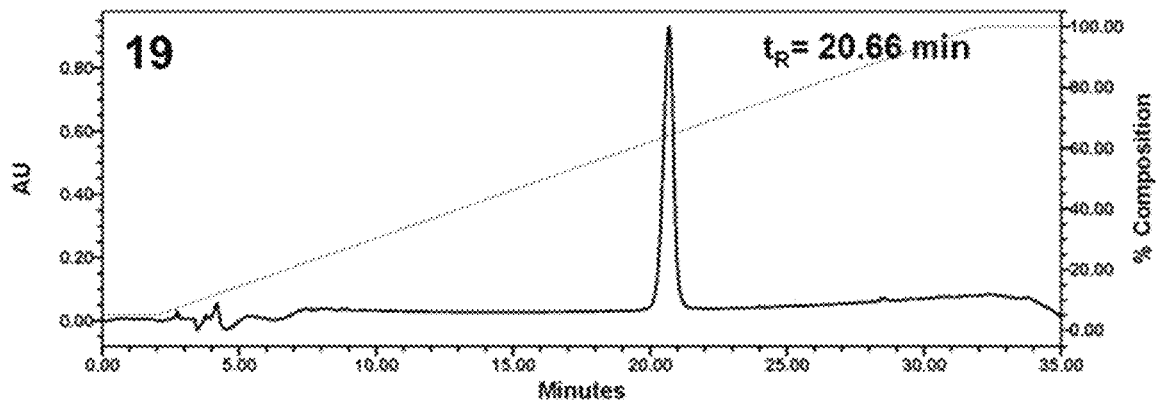
FIG. 22 is a diagram showing results of analysis for Peptoid NO. 19 purified through high-performance liquid chromatography.
Figure 23:
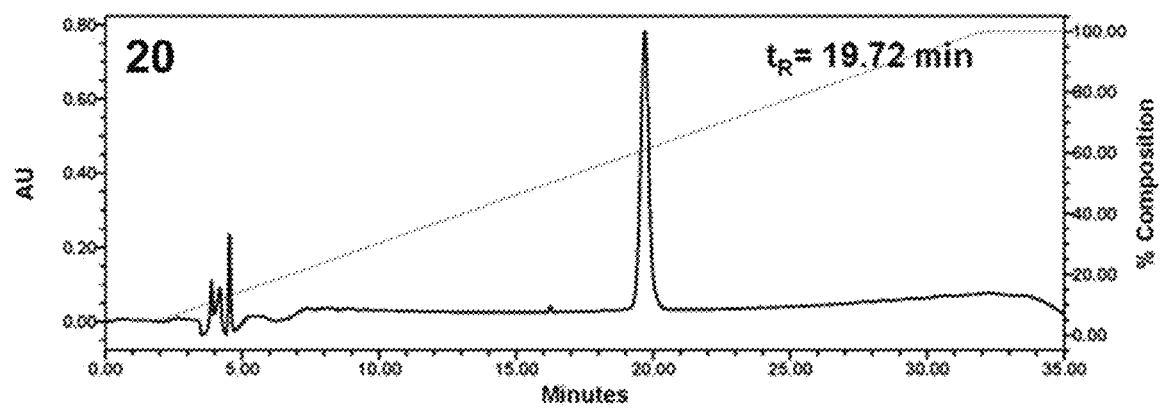
FIG. 23 is a diagram showing results of analysis for Peptoid NO. 20 purified through high-performance liquid chromatography.
Figure 24:
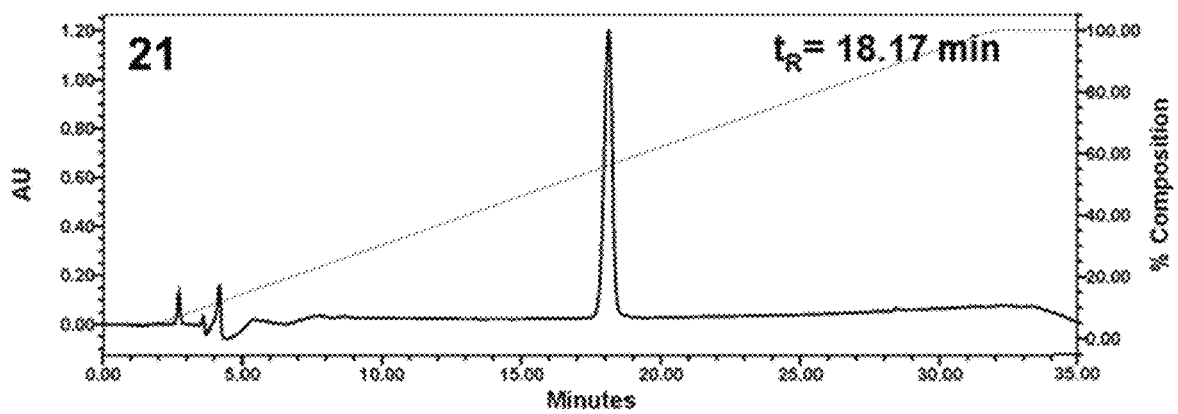
FIG. 24 is a diagram showing results of analysis for Peptoid NO. 21 purified through high-performance liquid chromatography.
Figure 25:
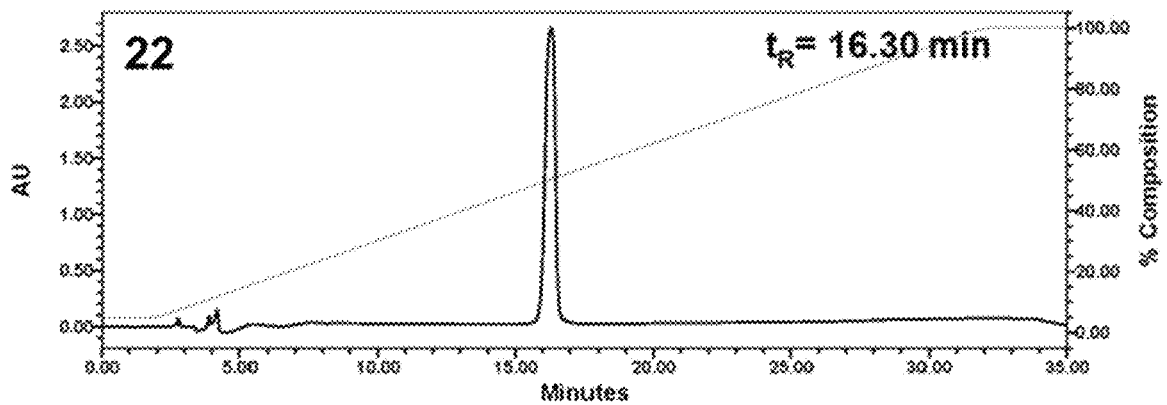
FIG. 25 is a diagram showing results of analysis for Peptoid NO. 22 purified through high-performance liquid chromatography.
Figure 26:
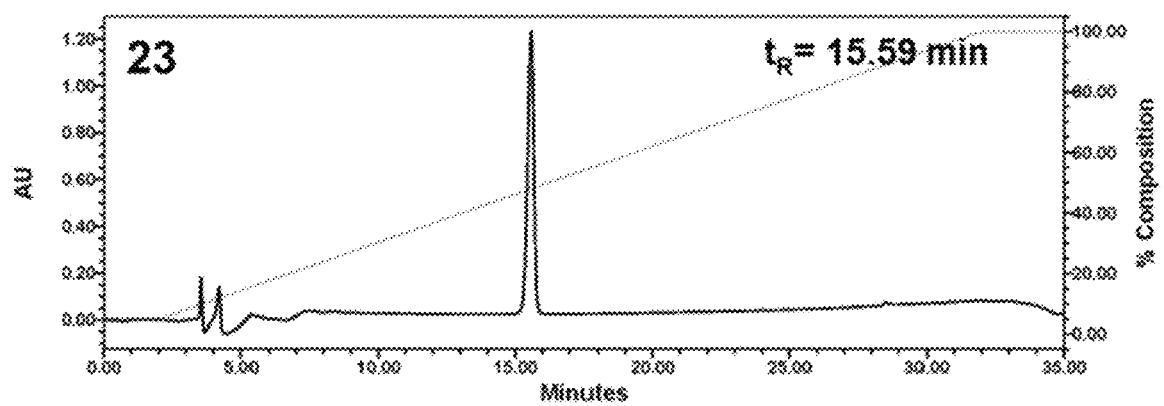
FIG. 26 is a diagram showing results of analysis for Peptoid NO. 23 purified through high-performance liquid chromatography.
Figure 27:
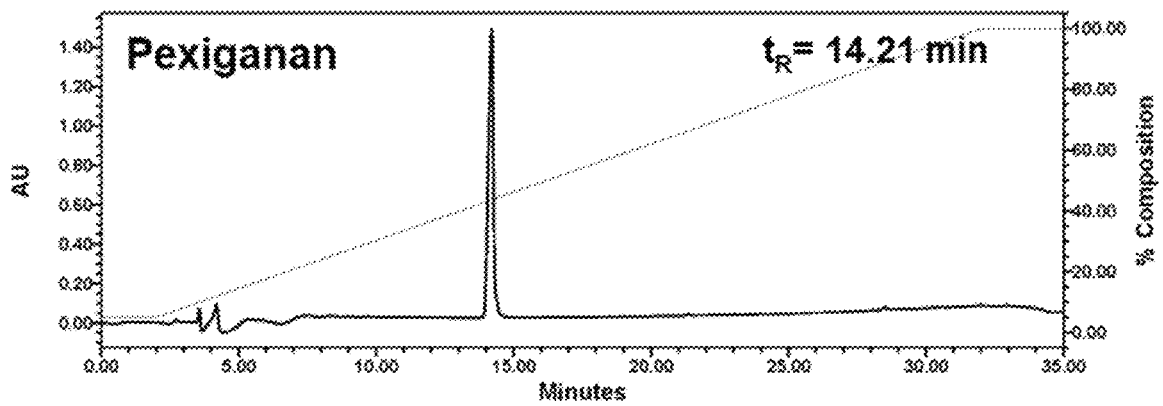
FIG. 27 is a diagram showing results of analysis for the peptide Pexiganan purified through high-performance liquid chromatography.

Under a condition in S9 fraction which is human liver tissue, it was identified that Peptoid NOS. 1 and 4 are present at 60% or more even after 24 hours has elapsed. On the other hand, Pexiganan was present at less than 1%. From these results, it was identified that Peptoid NOS. 1 and 4 have clearly superior metabolic stability as compared with Pexiganan. In addition, a remaining amount of Peptoid NO. 1 which is a control was about 64% after 24 hours had elapsed. However, a remaining amount of Peptoid NO. 4 was 74% after 24 hours had elapsed, indicating a higher stability (FIGS. 2A to 2C).

Analytic Example 1

Selectivity Analysis of Peptoids

In order to identify changes in selectivity depending on alteration of degree of folding in helical structure of peptoids, selectivity of each peptoid was calculated using the resultant values measured in the Experimental Examples 1 and 2. The selectivity was obtained by dividing the $HD_{10}$ value by the minimum inhibitory concentration for *E. coli* (Table 8).

TABLE 7

| NO. | P. aeruginosa (PA01) | P. aeruginosa (198B MDR) | E. coli (63103 ESBL) | S. aureus (ATCC25923) | S. epidermidis (ET-024 MRSA) |
|---|---|---|---|---|---|
| 1  | 3.1 to 6.3  | 3.1 to 6.3  | 1.6         | 1.6        | <0.8 to 0.8 |
| 2  | 6.3         | 6.3 to 12.5 | 12.5        | 3.1 to 6.3 | <0.8 to 0.8 |
| 4  | 6.3         | 6.3         | 6.3 to 12.5 | 3.1 to 6.3 | <0.8 to 0.8 |
| 11 | 6.3         | 6.3 to 12.5 | 6.3         | 3.1        | <0.8 to 0.8 |
| 13 | 6.3         | 6.3         | 6.3         | 3.1        | <0.8 to 0.8 |
| 15 | 3.1 to 6.3  | 6.3         | 6.3         | 3.1        | <0.8 to 0.8 |
| 17 | 6.3         | 6.3 to 12.5 | 6.3 to 12.5 | 3.1 to 6.3 | <0.8 to 0.8 |

TABLE 8

| NO. | Selectivity [$HD_{10}$/MIC (E. coli)] |
|---|---|
| 1 | 0.4 |
| 2 | >8.0 |
| 3 | 4.5 |
| 4 | 7.1 |
| 5 | 8.5 |
| 6 | 8.1 |
| 7 | 12.3 |
| 8 | 7.1 |
| 9 | 4.3 |
| 10 | 8.3 |
| 11 | 4.9 |
| 12 | 6.4 |
| 13 | 3.3 |
| 14 | 4.3 |
| 15 | 2.1 |
| 16 | 8.4 |
| 17 | 4.8 |

As shown in Table 8 above, high selectivity was exhibited for Peptoid NOS. 5, 6, 7, 10, and 16. Therefore, among Peptoid NOS. 1 to 17, Peptoid NOS. 5, 7, and 16 were selected as peptides having good antimicrobial activity and low red blood cell toxicity.

II. Identification of Changes in Activity of Peptoids Depending on Alteration in Cationic Residues of Peptoids

Production Example 2

Preparation of Peptoids with Altered Cationic Residues

Peptoid NOS. 18 to 23 with altered cationic residues were synthesized according to the formulae as shown in Table 9 below in the same manner as in the Preparation Example 1.

TABLE 9

| NO. | Formula (Pexiganan: Amino acid sequence) |
|---|---|
| 1 | H-(Nlys-Nspe-Nspe)$_4$-NH$_2$ |
| 18 | H-(Nlys-Nspe-Nspe)$_3$-NH$_2$ |
| 19 | H-(Nlys-Nspe(pCl)-Nspe(pCl))$_4$-NH$_2$ |
| 20 | H-(Nlys-Nspe(pCH$_3$)-Nspe(pCH$_3$))$_4$-NH$_2$ |
| 21 | H-(Nlys-Nspe(pF)-Nspe(pF))$_4$-NH$_2$ |
| 22 | H-(Nlys-Nspe-Nspe)$_4$-Mys-NH$_2$ |
| 23 | H-(Nlys-Nspe-Nspe)$_3$-Mys-NH$_2$ |
| Pexiganan | GIGKFLKKAKKFGKAFVKILKK-NH$_2$ |

The synthesized peptoids are shown in Table 10 below. In Table 10 below, Peptoid NO. 1 is a known peptoid and was constructed for the purposed of making a comparison with other peptoids in terms of antimicrobial activity and cytotoxicity.

TABLE 10

| NO. | Structural formula |
|---|---|
| 1 | |

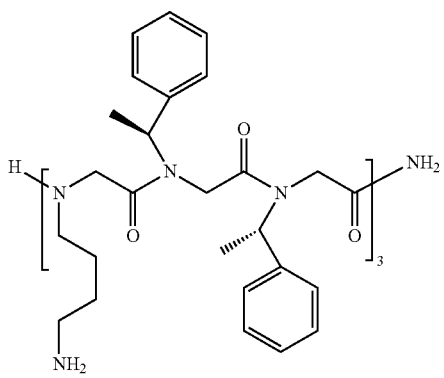

18

TABLE 10-continued
| NO. | Structural formula |
|---|---|
| 19 | 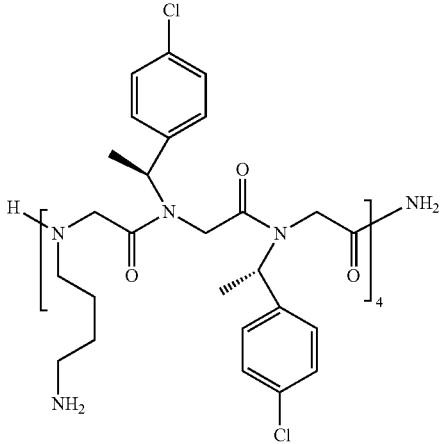 |
| 20 | 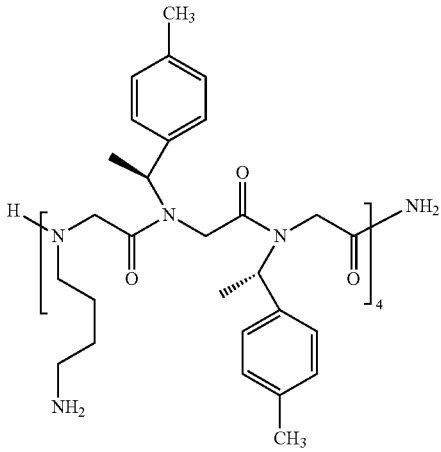 |
| 21 | 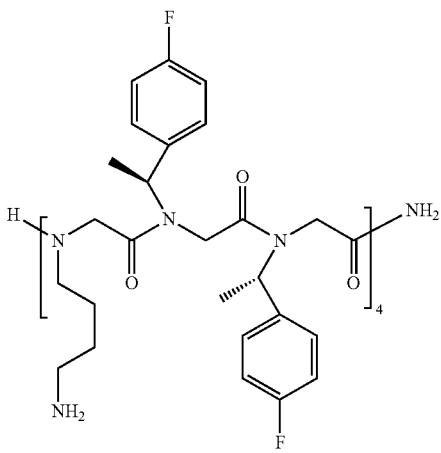 |

TABLE 10-continued

| NO. | Structural formula |
|---|---|
| 22 | (structure) |
| 23 | (structure) |

The synthesized Peptoid NOS. 1, 18 to 23, and the peptide Pexiganan were analyzed using HPLC and LC-MS. The HPLC and LC-MS analysis results are shown in Table 11 below and FIGS. 20 to 27.

TABLE 11

| NO. | Molecular weight (MW, Da) | Net charge | CTLR | HPLC elution (% CH$_3$CN) |
|---|---|---|---|---|
| 1 | 1819.36 | +4 | 0.33 | 53.6 |
| 18 | 1368.78 | +3 | 0.33 | 51.6 |
| 19 | 2094.90 | +4 | 0.33 | 64.1 |
| 20 | 1931.58 | +4 | 0.33 | 61.1 |
| 21 | 1963.29 | +4 | 0.33 | 56.2 |
| 22 | 1947.54 | +5 | 0.38 | 50.3 |
| 23 | 1496.96 | +4 | 0.40 | 48.0 |
| Pexiganan | 2477.22 | +9 | 0.41 | 43.7 |

Experimental Example 6

Identification of Antimicrobial Activity of Peptoids with Altered Cationic Residues In order to measure antimicrobial activity of the peptoids, Gram-positive B. subtilis or Gram-negative E. coli strain DH5α was treated with Peptoid NOS. 1, 18 to 23, and the peptide Pexiganan, and minimum inhibitory concentrations were measured. Peptoid NOS. 1 and 2, and the peptide Pexiganan are already known antimicrobial peptides and were used for the purpose of making a comparison with novel peptoids in terms of antimicrobial activity.

Specifically, B. subtilis or E. coli DHS a was inoculated into LB liquid medium, and cultured at a temperature of 37° C. for 18 hours. Thereafter, the bacteria were diluted with LB medium so that each bacterial number was 2×10$^5$ colony-forming units (CFU) per 1 mL, and dispensed into 96-well microtiter plates at 100 μL each. The peptoid, which is 2-fold serially diluted using sterile water, was added to each well at 100 μL each. The plates were incubated at a temperature of 37° C. for 18 hours.

Thereafter, absorbance was measured at a wavelength of 600 nm using a microplate reader (Bio-Rad). The lowest peptoid concentration that completely suppresses growth of microorganisms was measured by a minimum inhibitory concentration (MIC), and the measurement results are shown in Table 12 below. Each of the minimum inhibitory concentration values was calculated as an average value of numerical values obtained through three independent experiments.

TABLE 12

| | MIC (μM) | |
|---|---|---|
| NO. | B. subtilis | E. coli |
| 1 | 0.8 | 1.6 |
| 18 | 1.6 | 3.1 |
| 19 | 6.1 | >6.1 |

TABLE 12-continued

| | MIC (μM) | |
|---|---|---|
| NO. | B. subtilis | E. coli |
| 20 | 0.8 | >6.1 |
| 21 | 0.4 | 3.1 |
| 22 | 0.4 | 1.6 |
| 23 | 0.8 | 1.6 |
| Pexiganan | 0.4 | 0.8 |

As shown in Table 12 above, for *B. subtilis*, overall, low minimum inhibitory concentration values were measured for the other peptoids except Peptoid NO. 19 and Pexiganan. In addition, for *E. coli* DH5 α, low minimum inhibitory concentration values were measured for Peptoid NO. 1, 21, or 22, and Pexiganan.

Experimental Example 7

Identification of Hemolytic Activity of Peptoids

Hemolytic activity of Peptoid NOS. 1, 18 to 23, and the peptide Pexiganan was measured in the same manner as in Experimental Example 2. The results are shown in Table 13 below.

TABLE 13

| NO. | $HD_{10}/HD_{50}$ | $H_{max}$ (%) |
|---|---|---|
| 1 | 9.1/63.4 | 100 |
| 18 | 119.5/>200 | 38.7 ± 5.4 |
| 19 | <6.25/10.4 | 100 |
| 20 | <6.25/8.3 | 100 |
| 21 | <6.25/<6.25 | 100 |
| 22 | 19.5/>200 | 48.1 ± 3 |
| 23 | >200/>200 | 9.8 ± 0.8 |
| Pexiganan | 113.4/>200 | 21.5 ± 2.9 |

As shown in Table 13, low $HD_{10}$ and $HD_{50}$ values were measured for Peptoid NO. 1. On the other hand, a high-concentration $HD_{50}$ value was measured for Peptoid NO. 18, 22, or 23, and a high-concentration $HD_{10}$ value was identified for Peptoid NO. 18 or 23.

Experimental Example 8

Identification of Cytotoxicity of Peptoids against Human Cell Lines

In order to determine whether the peptoids were cytotoxic against human cell lines, MRCS cell line (Korean Cell Line Bank) which is a human lung cell line was cultured in a DMEM (Dulbecco's modified Eagle's medium) culture solution containing 10% (v/v) fetal bovine serum (FBS) at 5% $CO_2$ and a temperature of 37° C. 100 μL of DMEM medium was dispensed into each well of a 96-well microtiter plate so that the number of cells was $1.3 \times 10^4$, and then incubated overnight at a temperature of 37° C. in a 5% $CO_2$ incubator. In this case, a DMEM medium was used as a negative control. Thereafter, the peptoid which is 2-fold serially diluted using sterile water was added to each well, and then incubated for 24 hours.

After incubation, 20 μL of an MTS solution [3-(4,5-dimethylthiazol-2-yl)-5-(3-carboxymethoxyphenyl)-2-(4-sulfophenyl)-2H-tetrazolium, inner salt; MTS] was added thereto and incubated at a temperature of 37° C. for 4 hours. Thereafter, % survival was calculated by measuring absorbance at a wavelength of 490 nm using an ELISA reader. The % survival was calculated as a percentage obtained by dividing the absorbance value for a well-treated with the peptoid by the absorbance value for a well containing control cells which had not been treated with the peptoid. $LC_{50}$ values, which are concentrations of the peptoids indicating a survival rate of 50%, are shown in Table 14 below.

TABLE 14

| NO. | $LC_{50}$ (μM) |
|---|---|
| 1 | 8.0 |
| 18 | 40.0 |
| 19 | 3.0 |
| 20 | 8.0 |
| 21 | 9.5 |
| 22 | 10.0 |
| 23 | 80.5 |
| Pexiganan | 21.2 |

As shown in the above Table 14, overall, low cell survival rates were exhibited for the other peptoids except Peptoid NO. 23 and the peptide Pexiganan. On the other hand, a high cell survival rate which is $LC_{50}=80.5$ μM was exhibited for Peptoid NO. 23. In Table 14 above, LCso means a compound concentration indicating a cell survival rate of 50%.

What is claimed is:

1. A peptoid having any one formula selected from the following Formulae 1, 2 and 5:

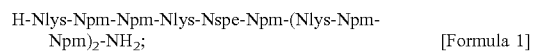

H-Nlys-Npm-Npm-Nlys-Nspe-Npm-(Nlys-Npm-Npm)$_2$-NH$_2$;  [Formula 1]

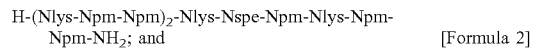

H-(Nlys-Npm-Npm)$_2$-Nlys-Nspe-Npm-Nlys-Npm-Npm-NH$_2$; and  [Formula 2]

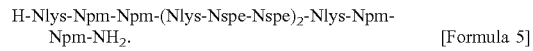

H-Nlys-Npm-Npm-(Nlys-Nspe-Nspe)$_2$-Nlys-Npm-Npm-NH$_2$.  [Formula 5]

2. An antimicrobial composition, comprising the peptoid of claim 1 as an active ingredient.

3. The antimicrobial composition according to claim 2, wherein the peptoid exhibits antimicrobial activity against Gram-positive bacteria or Gram-negative bacteria.

4. The antimicrobial composition according to claim 3, wherein the Gram-positive bacteria are bacteria of *Staphylococcus* sp., *Bacillus* sp., *Streptococcus* sp., or *Enterococcus* sp.

5. The antimicrobial composition according to claim 3, wherein the Gram-positive bacteria are *Staphylococcus aureus*, methicillin-resistant *Staphylococcus aureus* (MRSA), Quinolone-resistant *Staphylococcus aureus* (QRSA), vancomycin resistant enterococcus (VRE), vancomycin intermediate-resistant *Staphylococcus aureus* (VISA), *Bacillus subtilis*, *Bacillus cereus*, *Streptococcus pneumoniae*, *Enterococcus faecalis*, or *Staphylococcus epidermidis*.

6. The antimicrobial composition according to claim 3, wherein the Gram-negative bacteria are bacteria of *Salmonella* sp., *Acinetobacter* sp., *Escherichia* sp., *Pseudomonas* sp., or *Klebsiella* sp.

7. The antimicrobial composition according to claim 3, wherein the Gram-negative bacteria are *Salmonella typhimurium*, *Acinetobacter calcoaceticus*, *E. coli*, *Pseudomonas aeruginosa*, or *Klebsiella aerogenes*.

8. An antimicrobial quasi-drug composition, comprising the peptoid of claim 1 as an active ingredient.

9. A pharmaceutical composition for treating a bacterial infection, comprising the peptoid of claim 1 as an active ingredient.

10. The pharmaceutical composition according to claim 9, wherein the bacterial infection is any one selected from the group consisting of cholera, dysentery, pertussis, typhoid fever, laryngeal diphtheria, gland pest, pulmonary pest, scarlet fever, septicemia, pyoderma, pulmonary tuberculosis, joint tuberculosis, renal tuberculosis, tuberculous meningitis, enteritis, and food poisoning.

11. A method for treating a bacterial infection, comprising administering the peptoid according to claim 1 to a subject in need thereof.

\* \* \* \* \*